Figure 1:
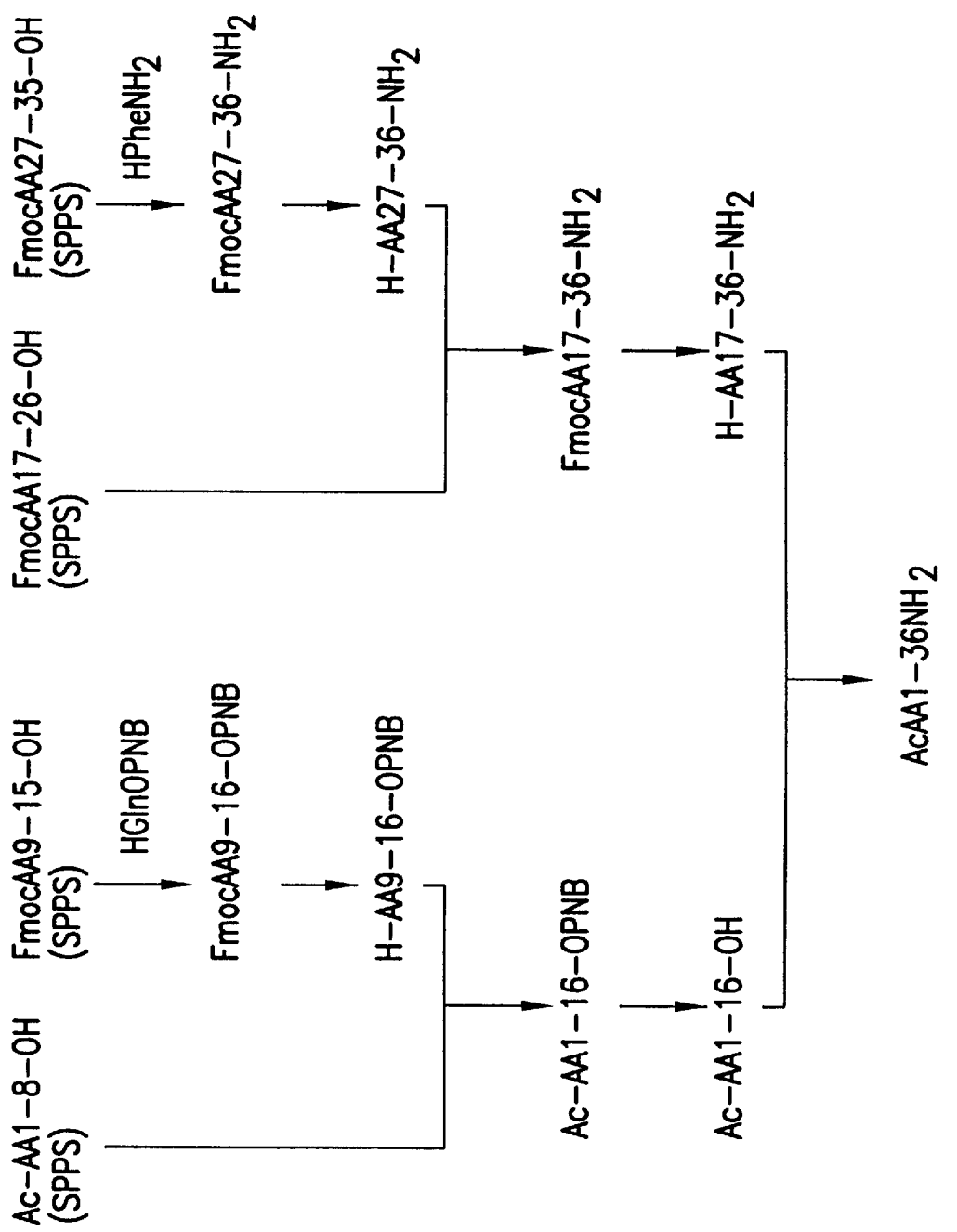

United States Patent
Kang et al.

[11] Patent Number: 6,015,881
[45] Date of Patent: Jan. 18, 2000

[54] METHODS AND COMPOSITIONS FOR PEPTIDE SYNTHESIS

[75] Inventors: Myung-Chol Kang, Chapel Hill; Brian Bray, Graham; Maynard Lichty; Catherine Mader, both of Durham; Gene Merutka, Hillsborough, all of N.C.

[73] Assignee: Trimeris, Inc.

[21] Appl. No.: 09/071,877

[22] Filed: May 1, 1998

Related U.S. Application Data

[63] Continuation-in-part of application No. 09/045,920, Mar. 23, 1998.
[51] Int. Cl.$^7$ .............................. A61K 38/00; C07K 5/00
[52] U.S. Cl. ......................... 530/339; 514/13; 514/14; 514/15; 514/16; 514/17; 514/12; 530/324; 530/325; 530/326; 530/327; 530/329; 530/333; 530/335; 530/338
[58] Field of Search ................................. 514/12, 13, 14, 514/15, 16; 530/324, 325, 326, 333, 335, 327, 329, 338, 339

[56] References Cited

U.S. PATENT DOCUMENTS

| | | | |
|---|---|---|---|
| 5,464,933 | 11/1995 | Bolognesi et al. | 530/324 |
| 5,656,480 | 8/1997 | Wild et al. | 435/325 |

FOREIGN PATENT DOCUMENTS

| | | |
|---|---|---|
| WO 94/28920 | 12/1994 | WIPO . |
| WO 96/19495 | 6/1996 | WIPO . |

OTHER PUBLICATIONS

Richter and Gadek, 1994, "A Surprising Observation about Mitsunobu Reactions in Solid Phase Synthesis", Tetrahedron Letters, 35:4705–4706.
Riniker et al., 1993, "A General Strategy for the Synthesis of Large Peptides: The Combined Solid–Phase and Solution Approach", Tetrahedron 49:9307–9320.
Sole and Barnay, 1992, "Optimization of Solid–Phase Synthesis of [Ala$^8$]–dynorphin A$^{1-3}$", J. Org. Chem. 57:5399–5403.
Kamber and Riniker, 1992, "The Solid Phase Synthesis of Protected Peptides Combined with Fragment Coupling in Solution", *Petides Chemistry and Biology* (Escom Science Publishers) pp. 525–526.
Barlos et al., 1989, "The Synthesis of Protected Peptide Fragments Using Substituted Triphenylmethyl Resins", Tetrahedron Letters 30:3943–3946.
Mergler et al., 1988, "Peptide Synthesis by a Combination of Solid–Phase and Solution Methods I: A New Very Acid Labile Anchor Group for the Solid Phase Synthesis of Fully Protected Fragments", Tetrahedron Letters 29:4005–4008.
Mergler et al., 1988, "Peptide Synthesis by a Combination of Solid–Phase and Solution Methods II Synthesis of Fully Protected Peptide Fragments on 2–Methoxy–4–Alkoxy–Benzyl Alcohol Resin", Tetrahedron Letters 29:4009–4012.
Sieber, 1987, "An Improved Method for Anchoring of 9–Fluorenylmethoxycarbonyl–Amino Acids to 4–Alkoxybenzyl Alcohol Resins", Tetrahedron Letters 28:6147–6150.
Creighton, 1993, *Proteins: Structures and Molecular Principles* (W.H. Freeman and Co., New York).
Carpino and Han, 1972, "The 9–Fluorenylmethoxycarbonyl Amino–Protecting Group", J. Org. Chem. 37:3404–3409.
Carpino and Han, 1970, "The 9–Fluorenylmethoxycarbonyl Function, a New Base–Sensitive Amino–Protecting Group", J. Am. Chem. Soc. 92:5748–5749.

*Primary Examiner*—Michael P. Woodward
*Assistant Examiner*—Anish Gupta
*Attorney, Agent, or Firm*—Pennie & Edmonds LLP

[57] ABSTRACT

The present invention relates, first, to methods for the synthesis of peptides, in particular T-20 (also referred to as "DP-178"; SEQ ID NO:1) and T-20-like peptides. Such methods utilize solid and liquid phase synthesis procedures to synthesize and combine groups of specific peptide fragments to yield the peptide of interest. The present invention further relates to individual peptide fragments which act as intermediates in the synthesis of the peptides of interest (e.g., T-20). The present invention still further relates to groups of such peptide intermediate fragments which can be utilized together to produce full length T-20 and T-20-like peptides.

44 Claims, 5 Drawing Sheets

SEQUENCE LISTING

<160> NUMBER OF SEQ ID NOS: 19

<210> SEQ ID NO 1
<211> LENGTH: 36
<212> TYPE: PRT
<213> ORGANISM: Human immunodeficiency virus

<400> SEQUENCE: 1

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
         35

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:peptide
      fragment

<400> SEQUENCE: 2

Tyr Thr Ser Leu Ile His Ser Leu
 1               5

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:peptide
      fragment

<400> SEQUENCE: 3

Tyr Thr Ser Leu Ile His Ser Leu Ile Glu Glu Ser Gln Asn Gln
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:peptide
      fragment

<400> SEQUENCE: 4

Tyr Thr Ser Leu Ile His Ser Leu Ile Glu Glu Ser Gln Asn Gln Gln
 1               5                  10                  15

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence:peptide
      fragment

<400> SEQUENCE: 5

Tyr Thr Ser Leu Ile His Ser Leu Ile Glu Glu Ser Gln Asn Gln Gln
 1               5                  10                  15

Glu Lys

-continued

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:peptide
      fragment

<400> SEQUENCE: 6

Ile Glu Glu Ser Gln Asn Gln
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:peptide
      fragment

<400> SEQUENCE: 7

Ile Glu Glu Ser Gln Asn Gln Gln
 1               5

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence:peptide
      fragment

<400> SEQUENCE: 8

Gln Glu Lys Asn Glu Gln Glu Leu Leu Glu Leu Asp Lys Trp Ala Ser
 1               5                  10                  15

Leu Trp Asn Trp
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence:peptide
      fragment

<400> SEQUENCE: 9

Gln Glu Lys Asn Glu Gln Glu Leu Leu Glu Leu Asp Lys Trp Ala Ser
 1               5                  10                  15

Leu Trp Asn Trp Phe
            20

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:peptide
      fragment

<400> SEQUENCE: 10

Glu Lys Asn Glu Gln Glu Leu
 1               5

<210> SEQ ID NO 11
<211> LENGTH: 10
<212> TYPE: PRT
<213> ORGANISM: Artificial Sequence
```

-continued

<220> FEATURE:
<223> OTHER INFORMATION: Description of Artificial Sequence:peptide
      fragment

<400> SEQUENCE: 11

Glu Lys Asn Glu Gln Glu Leu Leu Glu Leu
 1               5                  10

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence:peptide
      fragment

<400> SEQUENCE: 12

Glu Lys Asn Glu Gln Glu Leu Leu Glu Leu Asp Lys Trp Ala Ser Leu
 1               5                  10                  15

Trp Asn Trp Phe
            20

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence:peptide
      fragment

<400> SEQUENCE: 13

Asn Glu Gln Glu Leu Leu Glu Leu Asp Lys Trp Ala Ser Leu Trp Asn
 1               5                  10                  15

Trp

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence:peptide
      fragment

<400> SEQUENCE: 14

Asn Glu Gln Glu Leu Leu Glu Leu Asp Lys Trp Ala Ser Leu Trp Asn
 1               5                  10                  15

Trp Phe

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence:peptide
      fragment

<400> SEQUENCE: 15

Leu Glu Leu Asp Lys Trp Ala Ser Leu Trp Asn Trp
 1               5                  10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:peptide
      fragment

<400> SEQUENCE: 16

Leu Glu Leu Asp Lys Trp Ala Ser Leu Trp Asn Trp Phe
 1               5                  10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:peptide
      fragment

<400> SEQUENCE: 17

Asp Lys Trp Ala Ser Leu Trp Asn Trp
 1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:peptide
      fragment

<400> SEQUENCE: 18

Asp Lys Trp Ala Ser Leu Trp Asn Trp Phe
 1               5                  10

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence:peptide
      fragment

<400> SEQUENCE: 19

Glu Lys Asn Glu Gln Glu Leu Leu Glu Leu Asp Lys Trp Ala Ser Leu
 1               5                  10                  15

Trp Asn Trp

METHODS AND COMPOSITIONS FOR PEPTIDE SYNTHESIS

This application is a continuation-in-part of application Ser. No. 09/045,920, filed on Mar. 23, 1998.

1. INTRODUCTION

The present invention relates, first, to methods for the synthesis of peptides, in particular T-20 (also referred to as "DP-178"; SEQ ID NO:1) and T-20-like peptides. Such methods utilize solid and liquid phase synthesis procedures to synthesize and combine groups of specific peptide fragments to yield the peptide of interest. The present invention further relates to individual peptide fragments which act as intermediates in the synthesis of the peptides of interest (e.g., T-20). The present invention still further relates to groups of such peptide intermediate fragments which can be utilized together to produce full length T-20 and T-20-like peptides. The present invention still further relates to methods for the purification of peptides, in particular T-20 and T-20-like peptides, and the individual peptide fragments which act as intermediates in the synthesis of the subject peptides.

2. BACKGROUND

Recently, a large number of peptides have been identified which exhibit an ability to inhibit fusion-associated events, and, importantly, also exhibit potent antiviral activity. See, for example, U.S. Pat. Nos. 5,464,933; 5,656,480 and PCT Publication No. WO 96/19495T-20. As these peptides to extensively be used, as therapeutics, for example, the need arises for an ability to synthesize in large scale quantities.

While techniques exist for peptide synthesis, (see, e.g., Mergler et al., 1988, Tetrahedron Letters 29:4005–4008; Mergler et al., 1988, Tetrahedron Letters 29:4009–4012; Kamber et al. (eds), "Peptides, Chemistry and Biology, ESCOM, Leiden, 1992, 525–526; and Riniker et al., 1993, Tetrahedron Letters 49:9307–9320) no techniques currently exist which can be utilized for large scale, economical production of easily purified peptides such as T-20 and T-20-like peptides.

3. SUMMARY OF THE INVENTION

The present invention relates, first, to methods for the synthesis of peptides, in particular T-20 (also referred to as "DP-178"; SEQ ID NO:1) and T-20-like peptides. Such methods utilize solid and liquid phase synthesis procedures to synthesize and combine groups of specific peptide fragments to yield the peptide of interest. Generally, the methods of the invention comprise synthesizing specific side-chain protected peptide fragment intermediates of T-20 or a T-20-like peptide on a solid support, coupling the protected fragments in solution to form a protected T-20 or T-20-like peptide, followed by deprotection of the side chains to yield the final T-20 or T-20-like peptide. A preferred embodiment of the methods of the invention involves the synthesis of a T-20 peptide having an amino acid sequence as depicted in SEQ ID NO:1.

The present invention further relates to individual peptide fragments which act as intermediates in the synthesis of the peptides of interest (e.g., T-20). The peptide fragments of the invention include, but are not limited to, those having amino acid sequences as depicted in Table 1 below:

TABLE 1

| PEPTIDE NO. | AMINO ACID SEQUENCE | | CORRESPONDING NUMBERED AMINO ACID SEQUENCE OF T-20 |
|---|---|---|---|
| 1 | YTSLIHSL | (SEQ ID NO:2) | 1–8 |
| 2 | YTSLIHSLIEESQNQ | (SEQ ID NO:3) | 1–15 |
| 3 | YTSLIHSLIEESQNQQ | (SEQ ID NO:4) | 1–16 |
| 4 | YTSLIHSLIEESQNQQEK | (SEQ ID NO:5) | 1–18 |
| 5 | IEESQNQ | (SEQ ID NO:6) | 9–15 |
| 6 | IEESQNQQ | (SEQ ID NO:7) | 9–16 |
| 7 | QEKNEQELLELDKWASLWNW | (SEQ ID NO:8) | 16–35 |
| 8 | QEKNEQELLELDKWASLWNWF | (SEQ ID NO:9) | 16–36 |
| 9 | EKNEQEL | (SEQ ID NO:10) | 17–23 |
| 10 | EKNEQELLEL | (SEQ ID NO:11) | 17–26 |
| 11 | EKNEQELLELDKWASLWNWF | (SEQ ID NO:12) | 17–36 |
| 12 | NEQELLELDKWASLWNW | (SEQ ID NO:13) | 19–35 |
| 13 | NEQELLELDKWASLWNWF | (SEQ ID NO:14) | 19–36 |
| 14 | LELDKWASLWNW | (SEQ ID NO:15) | 24–35 |
| 15 | LELDKWASLWNWF | (SEQ ID NO:16) | 24–36 |
| 16 | DKWASLWNW | (SEQ ID NO:17) | 27–35 |
| 17 | DKWASLWNWF | (SEQ ID NO:18) | 27–36 |
| 18 | EKNEQELLELDKWASLWNW | (SEQ ID NO:19) | 17–35 |

The present invention still further relates to particular groups of peptide fragments which act as intermediates in the synthesis of the peptide of interest. The groups of peptide fragments according to the invention include Groups 1–20, as designated in Table 2 below.

TABLE 2

| Group | Amino Acid Sequence | | Corresponding Numbered Amino Acid Sequence of T-20 |
|---|---|---|---|
| 1 | YTSLIHSLIEESQNQQ | (SEQ ID NO:4) | 1–16 |
|  | EKNEQELLELDKWASLWNWF | (SEQ ID NO:12) | 17–36 |
| 2 | YTSLIHSLIEESQNQQ | (SEQ ID NO:4) | 1–16 |
|  | EKNEQELLEL | (SEQ ID NO:11) | 17–26 |
|  | DKWASLWNWF | (SEQ ID NO:18) | 27–36 |
| 3 | YTSLIHSLIEESQNQQ | (SEQ ID NO:4) | 1–16 |
|  | EKNEQELLEL | (SEQ ID NO:11) | 17–26 |
|  | DKWASLWNW | (SEQ ID NO:17) | 27–35 |

TABLE 2-continued

| Group | Amino Acid Sequence | | Corresponding Numbered Amino Acid Sequence of T-20 |
|---|---|---|---|
| 4 | YTSLIHSL | (SEQ ID NO:2) | 1–8 |
|  | IEESQNQ | (SEQ ID NO:6) | 9–15 |
|  | EKNEQELLELDKWASLWNWF | (SEQ ID NO:12) | 17–36 |
| 5 | YTSLIHSL | (SEQ ID NO:2) | 1–8 |
|  | IEESQNQ | (SEQ ID NO:6) | 9–15 |
|  | EKNEQELLEL | (SEQ ID NO:11) | 17–26 |
|  | DKWASLWNWF | (SEQ ID NO:18) | 27–36 |
| 6 | YTSLIHSL | (SEQ ID NO:2) | 1–8 |
|  | IEESQNQ | (SEQ ID NO:6) | 9–15 |
|  | EKNEQELLEL | (SEQ ID NO:11) | 17–26 |
|  | DKWASLWNW | (SEQ ID NO:17) | 27–35 |
| 7 | YTSLIHSL | (SEQ ID NO:2) | 1–8 |
|  | IEESQNQQ | (SEQ ID NO:7) | 9–16 |
|  | EKNEQELLELDKWASLWNWF | (SEQ ID NO:12) | 17–36 |
| 8 | YTSLIHSL | (SEQ ID NO:2) | 1–8 |
|  | IEESQNQQ | (SEQ ID NO:7) | 9–16 |
|  | EKNEQELLEL | (SEQ ID NO:11) | 17–26 |
|  | DKWASLWNWF | (SEQ ID NO:18) | 27–36 |
| 9 | YTSLIHSL | (SEQ ID NO:2) | 1–8 |
|  | IEESQNQQ | (SEQ ID NO:7) | 9–16 |
|  | EKNEQELLEL | (SEQ ID NO:11) | 17–26 |
|  | DKWASLWNW | (SEQ ID NO:17) | 27–35 |
| 10 | YTSLIHSLIEESQNQQ | (SEQ ID NO:4) | 1–16 |
|  | EKNEQEL | (SEQ ID NO:10) | 17–23 |
|  | LELDKWASLWNWF | (SEQ ID NO:16) | 24–36 |
| 11 | YTSLIHSLIEESQNQQ | (SEQ ID NO:4) | 1–16 |
|  | EKNEQEL | (SEQ ID NO:10) | 17–23 |
|  | LELDKWASLWNW | (SEQ ID NO:15) | 24–35 |
| 12 | YTSLIHSL | (SEQ ID NO:2) | 1–8 |
|  | IEESQNQ | (SEQ ID NO:6) | 9–15 |
|  | EKNEQEL | (SEQ ID NO:10) | 17–23 |
|  | LELDKWASLWNWF | (SEQ ID NO:16) | 24–36 |
| 13 | YTSLIHSL | (SEQ ID NO:2) | 1–8 |
|  | IEESQNQ | (SEQ ID NO:6) | 9–15 |
|  | EKNEQEL | (SEQ ID NO:10) | 17–23 |
|  | LELDKWASLWNW | (SEQ ID NO:15) | 24–35 |
| 14 | YTSLIHSL | (SEQ ID NO:2) | 1–8 |
|  | IEESQNQQ | (SEQ ID NO:7) | 9–16 |
|  | EKNEQEL | (SEQ ID NO:10) | 17–23 |
|  | LELDKWASLWNWF | (SEQ ID NO:16) | 24–36 |
| 15 | YTSLIHSL | (SEQ ID NO:2) | 1–8 |
|  | IEESQNQQ | (SEQ ID NO:7) | 9–16 |
|  | EKNEQEL | (SEQ ID NO:10) | 17–23 |
|  | LELDKWASLWNW | (SEQ ID NO:15) | 24–35 |
| 16 | YTSLIHSLIEESQNQ | (SEQ ID NO:3) | 1–15 |
|  | QEKNEQELLELDKWASLWNWF | (SEQ ID NO:9) | 16–36 |
| 17 | YTSLIHSLIEESQNQ | (SEQ ID NO:3) | 1–15 |
|  | QEKNEQELLELDKWASLWNW | (SEQ ID NO:8) | 16–35 |
| 18 | YTSLIHSLIEESQNQQEK | (SEQ ID NO:5) | 1–18 |
|  | NEQELLELDKWASLWNWF | (SEQ ID NO:14) | 19–36 |
| 19 | YTSLIHSLIEESQNQQEK | (SEQ ID NO:5) | 1–18 |
|  | NEQELLELDKWASLWNW | (SEQ ID NO:13) | 19–35 |
| 20 | YTSLIHSLIEESQHQQ | (SEQ ID NO:4) | 1–16 |
|  | EKNEQELLELDKWASLWNW | (SEQ ID NO:19) | 17–35 |

This invention is based, in part, on the inventors' unexpected discovery that certain combinations of solid phase liquid phase synthetic reactions allow high purity T-20 and T-20-like peptides to be manufactured for the first time on a large scale with high throughput and high yield. It has been found that by selecting the specific T-20 peptide fragments of the invention for solid phase synthesis, the highly efficient coupling of solid phase techniques may be exploited without having to use the 3-, 4- or even 5-fold excess of amino acids and reagents that are normally required in solid phase synthesis. The methods of the invention use only about a 1.5-fold of amino acid in the solid phase synthesis of the peptide fragments of the invention. This cost-saving reduction in the amount of amino acid and reagents makes the methods of the invention suitable for large scale synthesis of T-20 and T-20-like peptides.

In addition, the inventors have surprisingly found that certain peptide fragments may be synthesized in the solid phase at a loading of about 0.8 to 1 mmol per gram of solid phase resin. This loading is significantly greater than the loading range of 0.25 to 0.4 mmol per gram of resin typically achieved in solid phase peptide synthesis. Moreover, the inventors have found that synthesizing selected peptide fragments in the solid phase using super acid sensitive resin produces peptide fragments of unusually high purity. Chromatographic techniques are not necessary to purify the peptide fragments produced according to the invention; the fragments are simply put through precipitation and/or trituration steps before use, or used as obtained directly from the resin. Use of a super acid sensitive resin allows the synthesized, protected peptides of the invention to be cleaved from the resin without concomitant removal of the side-chain protecting groups. This reduces impurities, and allows peptides comprising 10 amino acids or greater to be synthesized in high purity. The impurity profile of T-20 and T-20-like peptides which are synthesized in the solution phase according to the methods of the invention by coupling of the high purity peptide fragments produced according to the invention consists of mainly fragments that did not couple, rather than closely related analogues. Accordingly, T-20 and T-20-like peptides produced according to the invention are much easier to purify than those produced according to conventional techniques. The Examples presented in Section 9, below, demonstrate such combinatorial syntheses of T-20 full length peptides.

The present inventors have also unexpectedly found that peptides such as T-20 and other T-20-like peptides, as well as certain peptide fragments described herein may be purified using high capacity materials which can be used at basic pH ranges. Thus, the present invention still further relates to methods for the purification of peptides, in particular T-20 and T-20-like peptides, and the individual peptide fragments which act as intermediates in the synthesis of the subject peptides.

3.1 DEFINITIONS

The amino acid notations used herein are conventional and are as follows:

Common Amino Acid Abbreviations

| Amino Acid | One-Letter Symbol | Common Abbreviation |
|---|---|---|
| Alanine | A | Ala |
| Asparagine | N | Asn |
| Aspartic acid | D | Asp |
| Glutamine | Q | Gln |
| Glutamic acid | E | Glu |
| Histidine | H | His |
| Isoleucine | I | Ile |
| Leucine | L | Leu |
| Lysine | K | Lys |
| Phenylalanine | F | Phe |
| Serine | S | Ser |
| Threonine | T | Thr |
| Tryptophan | W | Trp |
| Tyrosine | Y | Tyr |

4. BRIEF DESCRIPTION OF THE FIGURES

FIG. 1: T-20 four fragment approach. This figure depicts the scheme followed in the Example presented in Section 9.1, below, for the synthesis of full-length T-20 beginning with intermediate peptide fragment Group 6, as shown in Table 2, above.

Figure 2:
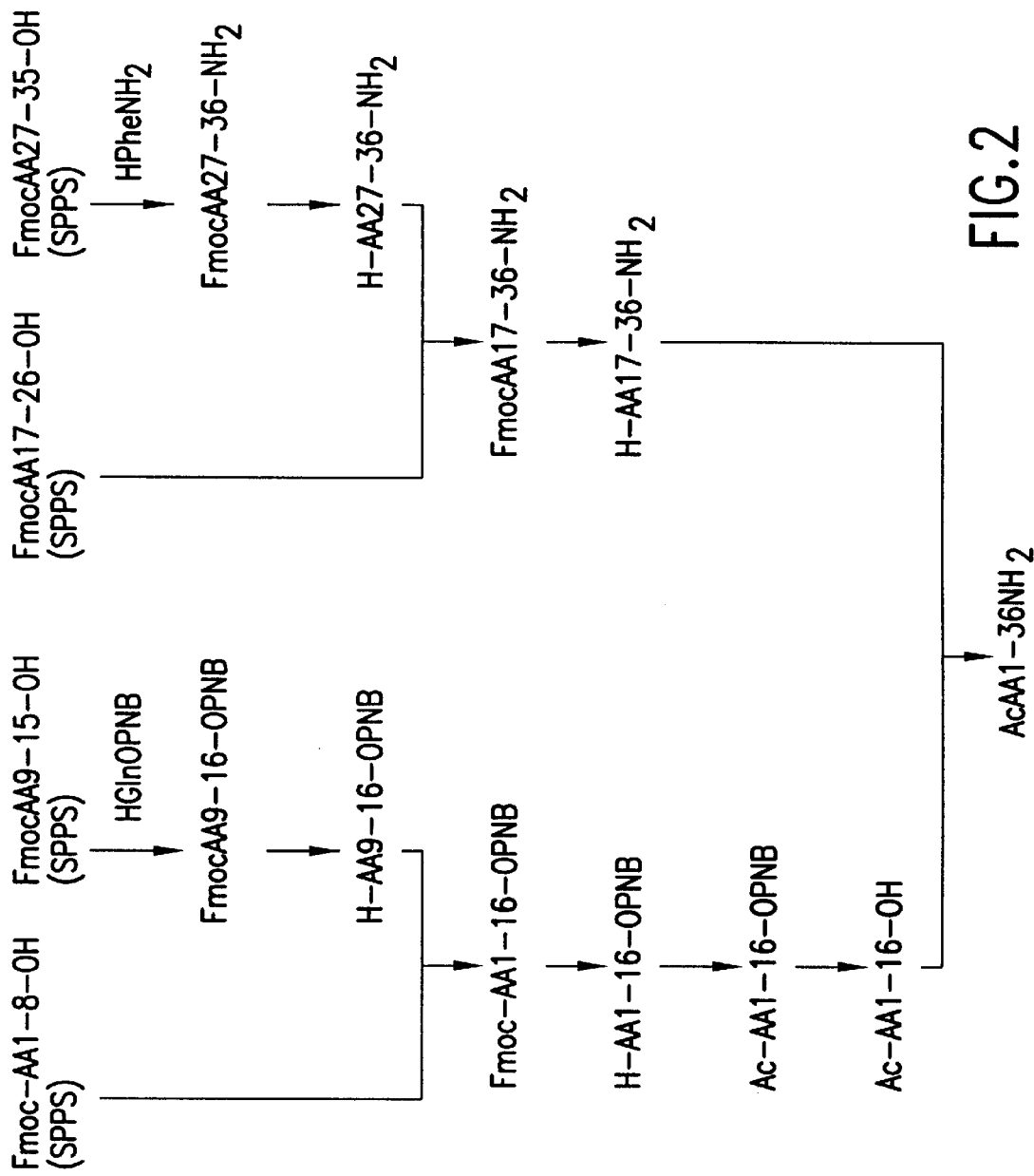

FIG. 2: T-20 four fragment approach, route 2. This figure depicts an additional four fragment scheme which couples peptide intermediate Group 6, as shown in Table 2, above, for the synthesis of full-length T-20.

Figure 3:
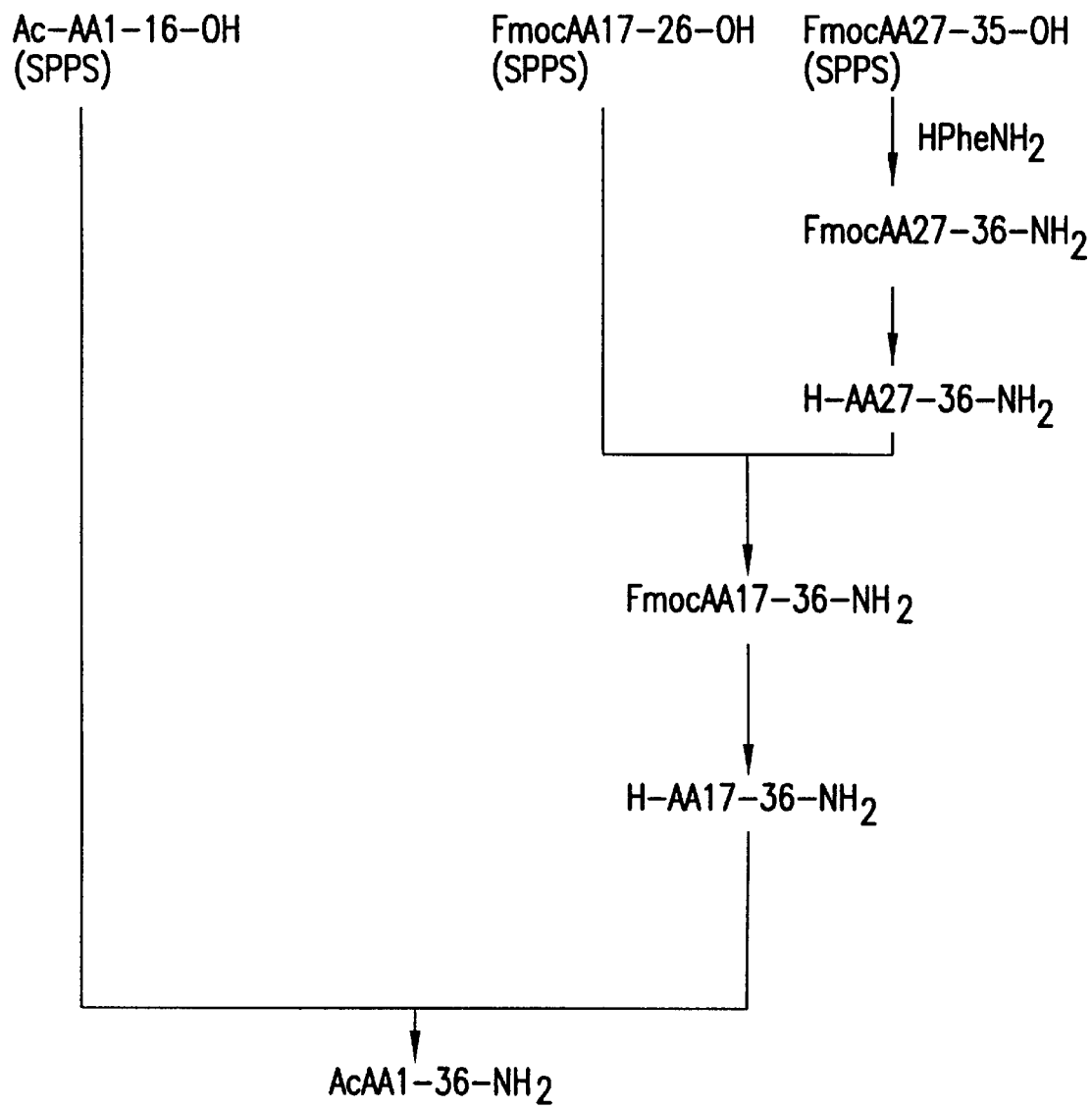

FIG. 3: T-20 three fragment approach. This figure depicts the scheme followed in the Example presented in Section 9.1, below, for the synthesis of full-length T-20.

Figure 4:
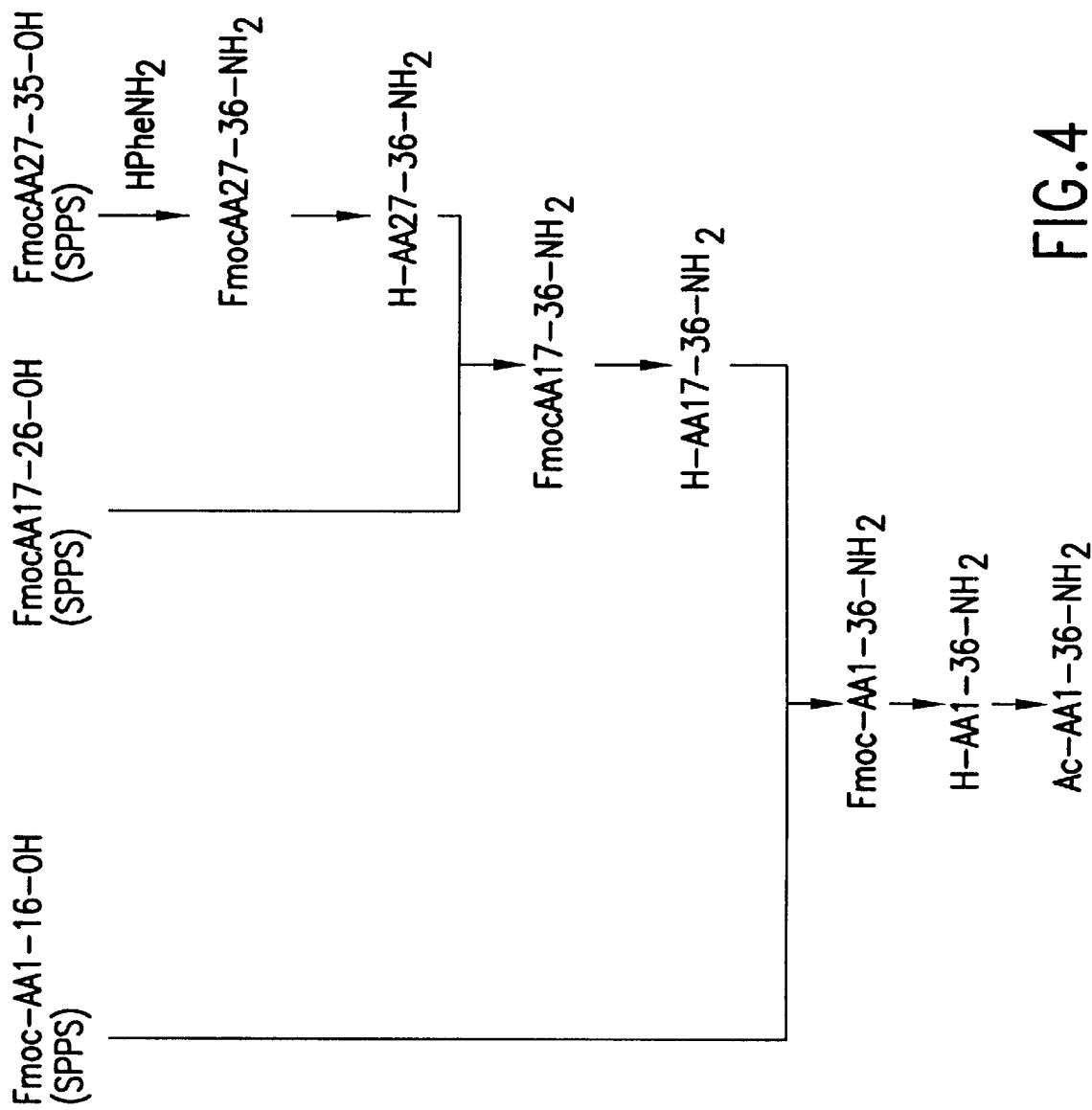

FIG. 4. T-20 three fragment approach, route 2. This figure depicts the scheme followed in the Example presented in Section 9.2, 9.3, 9.4 and 9.5, below, for the synthesis of full-length T-20.

Figure 5:
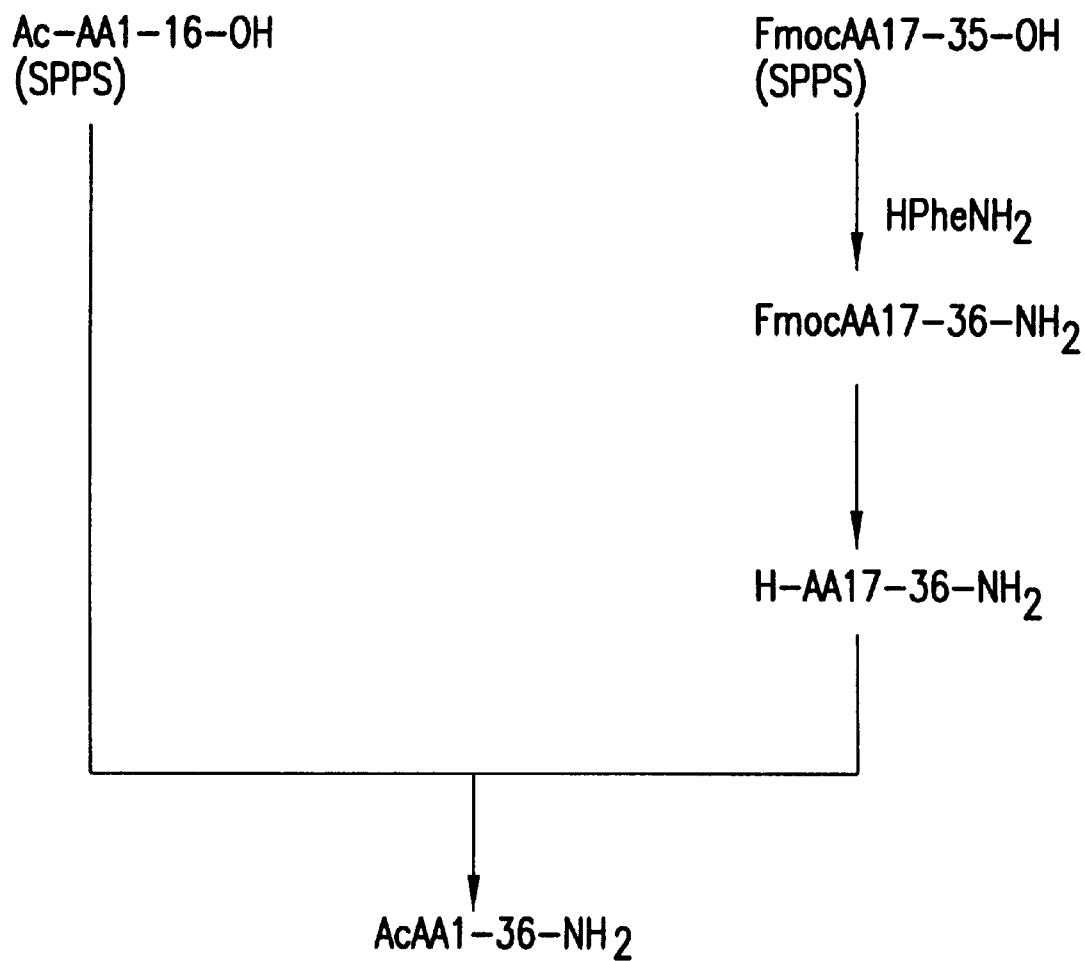

FIG. 5. T-20 two fragment approach. This figure depicts a scheme which couples peptide intermediate Group 18 as shown in Table 2, above, for the synthesis of full-length T-20.

5. DETAILED DESCRIPTION OF THE INVENTION

5.1 FULL LENGTH PEPTIDES

The present invention relates to methods, peptide fragments, groups of peptide fragments which can be used to synthesize the peptide known as T-20, or alternatively, DP-178. T-20 is a peptide which corresponds to amino acid residues 638 to 673 of the transmembrane protein gp41 from HIV-1$_{LAI}$ isolate and has the 36 amino acid sequence (reading from amino, NH$_2$, to carboxy, COOH, terminus):
NH$_2$-YTSLIHSLIEESQNQQEKNEQELLELDKWASLWNWF-COOH (SEQ ID NO:1)

It will be understood that the methods, fragments and groups of fragments and techniques utilized for choosing the fragments and groups of fragments of the present invention may be used to synthesize T-20-like fragments in addition to T-20. The term "T-20-like" as used herein means any HIV or non-HIV peptide listed in U.S. Pat. Nos. 5,464,933; 5,656,480 or PCT Publication No. WO 96/19495, each of which is hereby incorporated by reference in its entirety.

In addition to T-20 and the T-20-like peptides described above, the methods, fragments and groups of fragments of the present invention may be used to synthesize peptides having modified amino and/or carboxyl terminal ends. Taking T-20 as an example, such peptides can be of the formula:

X-YTSLIHSLIEESQNQQEKNEQELLELDKWASLWNWF-Z wherein X represents an amino group; a hydrophobic group selected from the group consisting of carbobenzoxyl, dansyl, and T-butyloxycarbonyl; an acetyl group; a 9-fluoroenyl-methoxy-carbonyl (FMOC) group; or a macromolecular carrier group selected from the group consisting of lipid-fatty acid conjugates, polyethylene glycol, and carbohydrates; and Z represents a carboxyl group; an amido group; a T-butyloxycarbonyl group; a para-nitrobenzyl ester group; or a macromolecular carrier group selected from the group consisting of lipid-fatty acid conjugates, polyethylene glycol, and carbohydrates. Techniques for addition of such "X" and "Z" groups are well known to those of skill in the art.

In a preferred embodiment, the methods of the invention are used to synthesize the peptide having the above formula wherein X is an acetyl group and Z is an amide group. The Examples presented in Section 9, below, demonstrate the successful synthesis of T-20 peptides via coupling of peptide intermediates described, below, in Section 5.2. In a preferred method, T-20 and T-20-like peptides and intermediates can be purified using any non-silica based column packing (for maximization of loading capacity) including but not limited to zirconium-based packings, poly-styrene, poly-acrylic or other polymer based packings which are stable at high (greater than >7) pH ranges. For example, among the non-silica-laded column packing exhibiting a broad pH range that includes pH valves greater than >> that are sold by Tosohaus (Montgomeryville, Pa.). Columns packed with such material can be run in low, medium or high pressure chromatography. See, for example, the purification method presented in Section 10, below.

5.2 PEPTIDE INTERMEDIATES

The present invention encompasses, but is not limited to, peptide fragment intermediates of T-20 and T-20-like peptides with specific amino acid sequences as listed in Table 1 above, and the groups of peptide fragment intermediates listed in tabLe 2. Such peptide intermediates, especially in groups as listed in Table 2, below, can be utilized to produce T-20 and T-20 like peptides.

Any one or more of the side-chains of the amino acid residues of peptide fragments listed in Table 1 or 2 may be protected with standard protecting groups such as t-butyl (t-Bu), trityl (trt) and t-butyloxycarbonyl (Boc). The t-Bu group is the preferred side-chain protecting group for amino acid residues Tyr(Y), Thr(T), Ser(S) and Asp(D); the trt group is the preferred side-chain protecting group for amino acid residues His(H), Gln(Q) and Asn(N); and the Boc group is the preferred side-chain protecting group for amino acid residues Lys(K) and Trp(W).

During the synthesis of fragments 1, 2, 3 and 4 listed in Table 1, the side-chain of the histidine residue must be protected, preferably with a trityl (trt) protecting group. If it is not protected, the acid used to cleave the peptide fragment from the resin will detrimentally react with the histidine residue, causing degradation of the peptide fragment.

Preferably, the glutamine residues of the peptide fragments of the invention are protected with trityl (trt) groups. However, it is preferred not to protect the glutamine residue at the carboxy-terminal end of fragments 1–16 and 9–16. It has been found that the absence of a protective group on the glutamine residue at the carboxy-terminal end of the 1–16 fragment facilitates reaction of the 1–16 fragment with the 17–36 fragment, allowing coupling of the fragments with only about 2% racemization. In addition, if lower solubility of any of the peptide fragments of the invention in organic solvents is desired, the trityl protecting groups may be eliminated from any one or more of the other glutamine residues of the fragments.

Preferably, all the asparagine residues of each peptide fragment of the invention are protected. In addition, it is preferred that the tryptophan residue is protected with a Boc group.

Protected peptide fragments according to peptide formulas 1–18 listed in Table 1 above include, but are not limited to, the compounds listed in Table 3 below.

TABLE 3

| Peptide Formula No. | Formula | Corresponding Numbered Amino Acid Sequence of T-20 |
| --- | --- | --- |
| 1a | Ac-YTSLIHSL-COOH (SEQ ID NO:2) | 1–8 |
| 1b | FMOC-YTSLIHSL-COOH (SEQ ID NO:2) | 1–8 |
| 3a | Ac-YTSLIHSLIEESQNQQ-OPNB (SEQ ID NO:4) | 1–16 |
| 3b | FMOC-YTSLIHSLIEESQNQQ-OPNB (SEQ ID NO:4) | 1–16 |
| 3c | Ac-YTSLIHSLIEESQNQQ-COOH (SEQ ID NO:4) | 1–16 |
| 3d | FMOC-YTSLIHSLIEESQNQQ-COOH (SEQ ID NO:4) | 1–16 |
| 5a | Ac-IEESQNQ-COOH (SEQ ID NO:6) | 9–15 |
| 5b | FMOC-IEESQNQ-COOH (SEQ ID NO:6) | 9–15 |
| 6a | NH$_2$-IEESQNQQ-OPNB (SEQ ID NO:7) | 9–16 |
| 6b | FMOC-IEESQNQQ-OPNB (SEQ ID NO:7) | 9–16 |
| 9a | Ac-EKNEQEL-COOH (SEQ ID NO:10) | 17–23 |
| 9b | FMOC-EKNEQEL-COOH (SEQ ID NO:10) | 17–23 |
| 10a | Ac-EKNEQELLEL-COOH (SEQ ID NO:11) | 17–26 |
| 10b | FMOC-EKNEQELLEL-COOH (SEQ ID NO:11) | 17–26 |
| 11a | NH$_2$-EKNEQELLELDKWASLWNWF-NH$_2$ (SEQ ID NO:12) | 17–36 |
| 11b | FMOC-EKNEQELLELDKWASLWNWF-NH$_2$ (SEQ ID NO:12) | 17–36 |
| 14a | Ac-LELDKWASLWNW-COOH (SEQ ID NO:15) | 24–35 |
| 14b | FMOC-LELDKWASLWNW-COOH (SEQ ID NO:15) | 24–35 |
| 15a | NH$_2$-LELDKWASLWNWF-NH$_2$ (SEQ ID NO:16) | 24–36 |
| 15b | FMOC-LELDKWASLWNWF-NH$_2$ (SEQ ID NO:16) | 24–36 |
| 16a | Ac-DKWASLWNW-COOH (SEQ ID NO:17) | 27–35 |
| 16b | FMOC-DKWASLWNW-COOH (SEQ ID NO:17) | 27–35 |
| 17a | NH$_2$-DKWASLWNWF-NH$_2$ (SEQ ID NO:18) | 27–36 |
| 17b | FMOC-DKWASLWNWF-NH$_2$ (SEQ ID NO:18) | 27–36 |
| 18A | FMOC-EKNEQELLELDKWASLWNW-COOH (SEQ ID NO:19) | 17–35 |

Any one or more of the side-chains of the amino acid residues of the peptides listed in Table 3 above may be protected with standard side-chain protecting groups such as tBu, trt and Boc, as described above. Representative synthesis of peptides from Table 3 are presented in Sections 7 and 8, below, which utilize the general techniques discussed in Section 5.4, below.

5.3 PEPTIDE SYNTHESIS

As discussed above, some of the individual peptide fragments of the invention are preferably made using solid phase synthesis techniques, while other peptides of the invention are preferably made using a combination of solid phase and solution phase synthesis techniques, said syntheses culminating in the production of T-20 or T-20-like peptides as described herein. However, it will be understood that the peptide fragments of the invention may be synthesized or prepared by techniques well known in the art. See, for example, Creighton, 1983, Proteins: Structures and Molecular Principles, W. H. Freeman and Co., N.Y., which is incorporated herein by reference in its entirety.

The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few.

In yet another embodiment of the invention, T-20 and T-20 like peptides comprising the sequences described above may be synthesized with additional chemical groups present at their amino and/or carboxy termini, such that, for example, the stability, reactivity and/or solubility of the peptides is enhanced. For example, hydrophobic groups such as carbobenzoxyl, dansyl, acetyl or t-butyloxycarbonyl groups, may be added to the peptides' amino termini. Likewise, an acetyl group or a 9-fluorenylmethoxy-carbonyl group may be placed at the peptides' amino termini. (See "X" modification of T-20, described above.) Additionally, the hydrophobic group, t-butyloxycarbonyl, or an amido group may be added to the peptides' carboxy termini. Similarly, a para-nitrobenzyl ester group may be placed at the peptides' carboxy termini. (See "Z" modification of T-20, described above.) Techniques for introducing such modifications are well known to those of skill in the art.

Further, T-20 and T-20-like peptides may be synthesized such that their steric configuration is altered. For example, the D-isomer of one or more of the amino acid residues of the peptide may be used, rather than the usual L-isomer.

Still further, at least one of the amino acid residues of the peptides of the invention may be substituted by one of the well known non-naturally occurring amino acid residues. Alterations such as these may serve to increase the stability, reactivity and/or solubility of the peptides of the invention.

Any of the T-20 or T-20-like peptides may be synthesized to additionally have a macromolecular carrier group covalently attached to their amino and/or carboxy termini. Such macromolecular carrier groups may include, for example, lipid-fatty acid conjugates, polyethylene glycol, carbohydrates or additional peptides. The "X" modification of T-20 described above may therefore additionally represent any of the above macromolecular carrier groups covalently attached to the amino terminus of a peptide, with an additional peptide group being preferred. Likewise, the "Z" modification of T-20 described above may additionally represent any of the macromolecular carrier groups described above.

Preferably, the peptide fragments of the present invention are synthesized by solid phase peptide synthesis (SPPS) techniques using standard FMOC protocols. See, e.g., Carpino et al., 1970, *J. Am. Chem. Soc.* 92(19):5748–5749; Carpino et al., 1972, *J. Org. Chem.* 37(22):3404–3409. In a preferred embodiment, the solid phase synthesis of the peptide fragments of the present invention is carried out on super acid sensitive solid supports which include, but are not limited to, 2-chlorotrityl chloride resin (see, e.g., Barlos et al., 1989, *Tetrahedron Letters* 30(30):3943–3946) and 4-hydroxymethyl-3-methoxyphenoxybutyric acid resin (see, e.g., Seiber, 1987, *Tetrahedron Letters* 28(49):6147–6150, and Richter et al., 1994, *Tetrahedron Letters* 35(27):4705–4706). Both the 2-chlorotrityl chloride and 4-hydroxymethyl-3-methoxyphenoxy butyric acid resins may be purchased from Calbiochem-Novabiochem Corp., San Diego, Calif.

General procedures for production and loading of resins which can be utilized in solid phase peptide synthesis are described herein. Resin loading can be performed, for example, via the following techniques: The resin, preferably a super acid sensitive resin such as 2-chlorotrityl resin, is charged to the reaction chamber. The resin is washed with a chlorinated solvent such as dichloromethane (DCM). The bed is drained and a solution of 1.5 equivalents of an amino acid and 2.7 equivalents of diisopropylethylamine (DIEA) in about 8–10 volumes of dichloroethane (DCE) is added. The N-terminus of the amino acid should be protected, preferably with Fmoc, and the side chain of the amino acid should be protected where necessary or appropriate. The mixture is agitated with nitrogen bubbling for 2 hours.

It should be noted that a chlorinated solvent is required for adequate swelling of the 2-chlorotrityl resin. Although DCE provides greater loading efficiency according to literature sources, DCM may be substituted with little or no reduction in the loading.

After agitation, the bed is drained and washed with DCM. The active sites on the resin are endcapped with a 9:1 MeOH:DIEA solution for about 20–30 minutes. The bed is drained, washed 4× with DCM and dried with a nitrogen purge to give the loaded resin.

Fmoc is the preferred protecting group for the N-terminus of the amino acid. Depending on which amino acid is being loaded, its side chain may or may not be protected. For example, when Trp is loaded, its side chain should be protected with Boc. Similarly, the side-chain of Gln may be protected with trt. However, when Gln is being loaded in preparation for the synthesis of the 1–16 peptide fragment, its side chain should not be protected. It is not necessary to protect the side-chain of Leu.

The Fmoc-protected amino acids used in loading the resin and in peptide synthesis are available, with or without side-chain protecting groups as required, from Sean or Genzyme. As an alternative to the above procedure, the resin may be purchased already loaded with the appropriate amino acid.

The Examples presented in Section 6, below, describe exemplary resin preparations.

Solid phase peptide synthesis techniques can be performed as, for example, according to the following techniques: The loaded resin is added to the reaction chamber and conditioned with a solvent, preferably methylene chloride (DCM; at preferably about 10 vol.) with nitrogen agitation for about 15 minutes to swell the resin beads. DCM is required for adequate swelling of the 2-chlorotrityl resin. The resin volume will double or triple in the reaction chamber as the beads swell and the active sites unfold and become accessible to reaction. After the resin is swelled, the solvent is drained from the reaction chamber.

Removal of the Fmoc (9-fluroenyl-methyloxycarbonyl) protecting group from the terminal amine or the resin is accomplished by treating the resin with 2 aliquots of a 20% solution of piperidine in N-methyl-2-pyrrolidinone (NMP) for about ten minutes each. The volume of the 20% solution of piperidine in NMP required for each aliquot will depend on the scale of the reaction being run. The resin is then washed 5–7 times with aliquots of NMP (about 10 vol.) to remove the Fmoc by-products (i.e., dibenzofulvene and its piperidine adduct) and residual piperidine.

A chloranil test may be used to determine if the removal of Fmoc by-products and residual pyridine is complete. The chloranil test solution is prepared by adding a drop of a saturated solution of chloranil in toluene to about 1 mL of acetone. The NMP washings may be tested by adding a drop of the washing to the chloranil test solution. A blue or violet color is a positive indication for the presence of secondary amine, indicating that Fmoc by-products and/or residual piperidine are still present. The NMP washing is repeated until the blue or violet color is no longer observed.

Meanwhile, the subsequent amino acid in the sequence to be added to the resin is activated for reaction at its carboxy terminus. The amine terminus of each amino acid should be protected with fmoc. Depending on which amino acid is being added, its side chain may or may not be protected. Preferably, the side-chains of tyr(Y), Thr(T), Ser(S) and Asp(P) are protected with t-Bu, the side-chains of His(H), Gln(Q) and Asn(N) are protected with trt, and the side-chains of Lys(K) and Trp(w) are protected with Boc. However, as discussed above, the side-chain of His must be protected. Moreover, it is preferred not to protect the side-chain of the Gln residue at the carboxy-terminal end of fragments 1–16 and 9–16. It is not necessary for the side-chains of Len or Ile to be protected.

The amino acid is activated as follows. The Fmoc-protected amino acid (1.5 eq), 1-hydroxybenzotriazole hydrate (HOBT) (1.5 eq), and diisopropyl-ethylamine (DIEA) (1.5 eq) are dissolved in NMP (about 7.5 vol.) at room temperature. The solution is chilled to 0–5° C., and then O-benzotriazol-1-yl-N,N,N',N'-tetramethyluronium hexafluorophosphate (HBTU) (1.5 eq) is added followed by stirring for 5–15 minutes to dissolve. It is important that activation is carried out at low temperature to minimize racemization of the amino acid. The HBTU is the last reagent added to the cold solution since activation and racemization cannot take place in its absence.

The solution of activated amino acid is charged to the drained resin, washing in with DCM (~2.5 vol). Note that activation of the amino acid is carried out in NMP due to the insolubility of HBTU in DCM. However, DCM is added to the reaction at this point to maintain adequate swelling of the resin beads. The reaction is agitated with $N_2$ bubbling for about 1 hour. Coupling completion may be monitored with a qualitative ninhydrin test as described below.

To check for completion of the reaction using the qualitative ninhydrin test, a 2–20 mg sample of the resin is withdrawn and washed clean with methanol. To the sample is added 3 drops of a 76% solution of phenol in ethanol, 4 or 5 drops of a 0.2 mM KCN solution in pyridine, and 3 drops of a 0.28 M solution of ninhydrin in ethanol. The sample is diluted with ethanol to a volume of about 0.5 mL and placed in a heat block at about 75° C. for 5–10 minutes. A blue or violet color is a positive indication for the presence of free amines, indicating that the reaction is not yet complete. The sample can be diluted further to a volume of about 3 mL to more easily gauge the degree of color change in the concentrated sample.

If a positive ninhydrin test is observed after one hour, the coupling reaction is continued for an additional hour. If the positive ninhydrin test persists after 2 hours, the resin is drained, washed three times in approximately 10 volumes of NMP, and the coupling reaction is repeated using 1 equivalent of activated amino acid.

If the resin is to be stored overnight between coupling cycles, the resin bed may be drained and covered with DCM under a nitrogen blanket. Alternatively, the bed may be drained, stored under a nitrogen blanket, then conditioned with a DCM wash prior to proceeding with the next coupling cycle. If the completed fragment is to be stored overnight prior to cleavage, the resin bed should be washed free of NMP with DCM because significant Fmoc deprotection can occur in NMP.

After the coupling is judged complete, the resin is drained and washed with 3 aliquots (approximately 10 vol.) of NMP. The cycle is repeated for subsequent mers of the peptide fragment. Following the final coupling reaction, the resin is washed with 4 aliquots (about 10 vol.) of NMP, then with 4 aliquots (approximately 10 vol.) of DCM. The resin-bound peptide may be dried with a nitrogen purge.

Peptides synthesized via solid phase synthesis techniques can be cleaved and isolated according to, for example, the following techniques: The peptide may be cleaved from the resin using techniques well known to those skilled in the art. For example, solutions of 1% or 2% trifluoroacetic acid (TFA) in DCM or a combination of a 1% and a 2% solution of TFA in DCM may be used to cleave the peptide. Acetic acid (HOAC) may also be used to cleave the peptide. The specific cleavage reagent, solvents and time required for cleavage will depend on the particular peptide being cleaved. After cleavage the cleavage fractions are subjected to standard work-up procedures to isolate the peptide. Typically, the combined cleavage fractions are concentrated under vacuum, followed by reconstitution with a solvent such as ethanol, methanol or heptane. In general, the peptide is precipitated by the addition of water, and collected by vacuum filtration. Alternatively, the product may be triturated prior to isolation of the peptide.

The Examples presented in Sections 7.1–7.6, below, present solid phase syntheses of peptide intermediates as shown in Tables 1, 2 and/or 3.

For synthesis of full length T-20 peptides, the peptide intermediates of Table 1, above, can be coupled together to yield the T-20 peptide. For example, the groups of peptide intermediates listed in Table 2, above, can be coupled together to produce T-20 full-length peptide. Representative examples of such synthesis of full-length T-20 from intermediate peptide fragments are presented in Section 9, below, and are depicted schematically in FIGS. 1–5.

In certain embodiments, a four fragment approach for synthesis of T-20 can be followed. A "four fragment approach" synthesis refers to a T-20 synthesis scheme which begins with four T-20 intermediate peptide fragments that are synthesized and coupled using solid and liquid phase synthesis techniques into a full-length T-20 peptide. Intermediate peptide fragment groups 5, 6, 8, 9 and 12–15 shown in Table 2, above, represent preferred groups. FIGS. 1 and 2 depict two four fragment approaches which utilize Table 2 peptide intermediate Group 6 to synthesize full-length T-20. For this group, it is noted that amino acid residue 36 (the T-20 carboxy 1-terminal amino acid residue) is introduced individually during the fragment coupling process. The culmination of the T-20 synthesis scheme shown in FIG. 1 is demonstrated in the example presented in Section 9.1.

In addition, embodiments, a three fragment approach for synthesis of T-20 can be followed. A "three fragment approach" synthesis refers to a T-20 synthesis scheme which begins with three T-20 intermediate peptide fragments that are synthesized and coupled using solid and liquid phase synthesis techiques into a full-length T-20 peptide. Intermediate fragment groups 2–4, 7, 10 and 11 shown in Table 2, above, represent preferred three fragment groups. FIGS. 3 and 4 depict two three fragment approaches which utilize Table 2 peptide intermediate Group 3 to synthesize full-length T-20. For this group, it is noted that amino acid residue 36 (the T-20 carboxyl-terminal amino acid residue) is introduced individually during the fragment coupling process. The culmination of the T-20 synthesis scheme shown in FIG. 3 is demonstrated in the example presented in Section 9.1, below. The culmination of the T-20 synthesis scheme shown in FIG. 4 is demonstrated in the examples presented in Sections 9.2–9.5, below.

In additional embodiments, a two fragment approach for synthesis of T-20 can be followed. A "two fragment approach" synthesis refers to a T-20 synthesis scheme which begins with two T-20 intermediate peptide fragments that are synthesized and coupled using solid and liquid phase synthesis techniques into a full-length T-20 peptide. Intermediate fragment Groups 1 and 16–20 shown in Table 2, above, represent preferred to fragment groups. FIG. 5 depicts a two fragment approach which utilizes Table 2 peptide intermediate Group 20 to synthesize full-length T-20. For this group, it is noted that amino acid residue (the T-20 carboxyl-terminal amino acid residue) is introduced individually during the fragment coupling process.

Solution phase peptide synthesis techniques well known to those of skill in the art may be utilized for synthesis of the peptide intermediate fragments of the invention. The Examples presented in Sections 8.1–8.11 describe exemplary solution phase peptide syntheses of peptide intermediates listed in Tables 1, 2 and/or 3. For example, among the non-silica-laded column packing exhibiting a broad pH range that includes pH valves greater than >> that are sold by Tosohaus (Montgomeryville, Pa.).

6. EXAMPLE

Resin Syntheses

Described herein, in Sections 6.1–6.3, are examples in which chlorotrityl resins are synthesized which can be utilized in conjunction with solid phase synthesis of the peptides and peptide intermediates described herein.

6.1 Preparation of Fmoc-Trp (Boc)-2-Chlorotrityl Resin

| Materials: | MW | eq | mmoles | grams | mL |
|---|---|---|---|---|---|
| 2-Chlorotritylchloride resin | — | 1.0 | 25 | 25 | — |
| Fmoc-Trp (Boc) -OH | — | 526.60 | 1.5 | 37.5 | 19.7 |
| Diisopropylethyl amine (DIEA) | 129.25 | 1.7 | 42.5 | 5.5 | 7.4 |
| Dichloroethane (DCE) | — | — | — | — | 250 |
| Dichloromethane (DCM) | — | — | — | — | 6 × 250 |

Procedure:

The 2-chlorotrityl chloride resin (25 g, 1 eq.) was charged to a 500 mL peptide chamber and washed with 250 mL of DCM. The bed was drained and a solution of the Fmoc-Trp (Boc)-OH (1.5 eq) and the DIEA (1.7 eq) in 10 volumes of DCE was added. The mixture was agitated with nitrogen bubbling for 2 hrs.

The bed was drained and washed with 250 mL DCM. The active sites on the resin were end-capped with 200 mL of a 9:1 MeOH:DIEA solution for 20 minutes. The bed was drained, washed with 4×250 mL of DCM, and dried with a nitrogen purge to give 34.3 g of loaded resin.

Quantitative HPLC analysis was performed by cleaving the Fmoc-amino acid from the resin and assaying versus a standard. HPLC assay of the material showed a loading of the resin at 0.68 mmol/g.

Column: Phenomenox Jupiter C18; 300 Å; 5μ

Flow rate: 1 mL/min

Detection: UV at 260 nm

Mobile phase:
  A: 0.1% aqueous TFA
  B: 0.1% TFA in acetonitrile 65% B isocratic Retention time: ~14 minutes

6.2 Preparation of Fmoc-Gln-2-Chlorotrityl Resin

| Materials: | MW | eq | mmoles | grams | mL |
|---|---|---|---|---|---|
| 2-Chlorotritylchloride resin | — | 1.0 | 25 | 25 | — |
| Fmoc-Gln-OH | 368.39 | 1.5 | 37.5 | 13.8 | — |
| Diisopropylethyl amine (DIEA) | 129.25 | 1.7 | 42.5 | 5.5 | 7.4 |
| Dichloroethane (DCE) | — | — | — | — | 75 |
| N,N-Dimethylformamide (DMF) | — | — | — | — | 200 |
| Dichloromethane (DCM) | — | — | — | — | 6 × 250 |
| 9:1 Methanol:DIEA | — | — | — | — | 200 |

Procedure:

The procedure used in the Example presented in 6.1, above, was repeated using a solution of Fmoc-Gln-OH (1.5 eq) and DIEA (1.7 eq.) in a mixture of 75 ml DCE and 200 ml DMF. The addition of DMF to stabilizes the Fmoc-Gln-OH. The reaction yielded 33.8 g of loaded resin. A theoretical loading of the resin at 0.74 mmol/g was assumed and the material was carried forward.

6.3 Preparation of Fmoc-Leu-2-Chlorotrityl Resin

| Materials: | MW | eq | mmoles | grams | mL |
|---|---|---|---|---|---|
| 2-Chlorotritylchloride resin | — | 1.0 | 250 | 250 | — |
| Fmoc-Leu-OH | 353.42 | 1.5 | 375 | 132.5 | — |
| Diisopropylethyl amine (DIEA) | 129.25 | 1.7 | 425 | 55 | 75 |
| Dichloroethane (DCE) | — | — | — | — | 2000 |
| Dichloromethane (DCM) | — | — | — | — | 6 × 1500 |
| 9:1 Methanol:DIEA | — | — | — | — | 1500 |

Procedure:

The resin was charged to a 3 L peptide chamber and washed with 1.5 DCM. The bed was drained and a solution of the Fmoc-Leu-OH (1.5 eq) and the DIEA (1.7 eq) in 8 volumes of DCE was added. The mixture was agitated with nitrogen bubbling for 2 hrs.

The bed was drained and washed with 1.5 L DCM. The active sites on the resin were end-capped with 1.5 L of a 9:1 MeOH:DIEA solution for 30 minutes. The bed was drained, washed with 4×1.5 L of DCM, and dried with a nitrogen purge to give 345 g of loaded resin.

Quantitative HPLC analysis was performed by cleaving the Fmoc-amino acid from the resin and assaying versus a standard. HPLC assay of the material showed a loading of the resin at 0.72 mmol/g.

Column: Phenomenox Jupiter C18; 300 Å; 5$\mu$

Flow rate: 1 mL/min

Detection: UV at 260 nm

Mobile phase:
  A: 0.1% aqueous TFA
  B: 0.1% TFA in acetonitrile 65% B isocratic Retention time: ~8 minutes

7. EXAMPLE

SOLID PHASE SYNTHESIS OF PEPTIDES

Presented below, in Sections 7.1–7.6, are examples of the solid phase synthesis of peptide intermediates as listed in Tables 1, 2, and/or 3.

7.1 Preparation of Fragment Fmoc-AA(1-8)-OH (Fragment 1b) Structure

Fmoc-Tyr(tBu)-Thr(tBu)-Ser(tBu)-Leu-Ile-His(trt)-Ser(tBu)-Leu-OH (SEQ ID NO:2)

|  | $C_{93}H_{121}N_{10}O_{15}$ MW 1619.06 | | | | |
|---|---|---|---|---|---|
| Materials: | MW | eq | mmoles | grams | mL |
| Fmoc-Leu-2-chlorotrityl resin | — | 1.0 | 15.6 | 20.0 | — |
| Fmoc-amino acid* | — | 1.5 | 23.4 | — | — |
| 1-Hydroxybenzotriazole (HOBT) hydrate* | 153.15 | 1.5 | 23.4 | 3.6 | — |
| O-Benzotriazol-1-yl-N,N,N',N'-tetramethyluronium hexafluorophosphate (HBTU)* | 379.25 | 1.5 | 23.4 | 8.9 | — |
| Diisopropylethylamine (DIEA)* | 129.25 | 1.5 | 23.4 | 3.0 | 4.1 |
| N-methyl-2-pyrrolidinone (NMP)* | — | — | — | — | 150 |
| Methylene chloride (DCM)* | — | — | — | — | 50 |
| 20% piperidine/NMP* | — | — | — | — | 2 × 200 |
| NMP for rinsing* | — | — | — | — | 200 (per wash) |
| 1% Trifluoroacetic acid (TFA) in DCM | — | — | — | — | 300 |
| 0.5% TFA/DCM | — | — | — | — | 200 |
| Pyridine | — | — | — | — | — |
| Ethyl alcohol | — | — | — | — | 110 |
| Water | — | — | — | — | 200 + 100 |

*per coupling cycle
Theoretical Yield: 25.3 g
Expected Yield: 80–90%
Actual Yield: 20.0 g Procedure:

To a 1 L peptide reaction chamber was charged 20.0 g Fmoc-Leu-2-chlorotrityl resin. The resin was conditioned in 200 mL (~10 vol) of DCM with nitrogen agitation for about 15 minutes to swell the beads, then drained.

Fmoc (9-fluorenylmethyloxycarbonyl) removal from the terminal amine was accomplished using 2×200 mL of a 20% solution of piperidine in NMP for 10 minutes each. The resin was then washed 5–7 times with 200 mL (~10 vol) of NMP to remove Fmoc by-products (dibenzofulvene and its piperidine adduct) and residual piperidine, as determined by a negative chloranil test.

Meanwhile, Fmoc-Ser (tBu), the subsequent amino acid in the sequence was activated for reaction at the carboxyl terminus. The Fmoc-protected amino acid (1.5 eq), the HOBT (1.5 eq), and the DIEA (1.5 eq) were dissolved in 150 mL (~7.5 vol) of NMP at room temperature. The solution was chilled to 0–5° C., then the HBTU (1.5 eq) was added and stirred 5–15 minutes to dissolve. The solution of activated acid was charged to the drained resin, washing in with 50 mL of DCM (~2.5 vol). The reaction was agitated with $N_2$ bubbling for 1 hr. Coupling completion was monitored with the qualitative ninhydrin test. After the coupling reaction was judged complete, the resin was drained and washed 3×200 mL (1 vol) of NMP.

The cycle was repeated for subsequent mers of the peptide fragment using 1.5 equivalents each of Fmoc-protected amino acids His(trt), Ile, Leu, Ser(tBu), Thr(tBu) and Tyr (tBu). Following the final coupling reaction, the resin was washed 4×200 mL (10 vol) of NMP, then with 4×200 mL (10 vol) of DCM. The resin was dried with a nitrogen purge to give 42 g of resin-bound peptide.

The peptide was cleaved from a 21 g quantity of the resin using 300 mL of 1% TFA in DCM for about 2 minutes, followed by 200 mL of 0.5% TFA in DCM. The cleavage fractions were collected onto pyridine (1:1 volume ratio to TFA). The cleavage washes were combined and concentrated under vacuum to a volume of ~50 mL, then reconstituted with 110 mL of ethanol while the concentration was continued to remove residual DCM to a final volume of ~250 mL. Product was precipitated with the addition of 200 mL of water. The slurry was stirred at room temperature for 30 minutes. The solids were collected by vacuum filtration and washed with ~100 mL of water. The product was air dried to give 20.0 g (79%) of Fmoc-AA(1-8)-OH of 95% HPLC purity.

Column: Phenomenox Jupiter C18

Flow rate: 1 mL/min

Detection: UV at 260 nm

Mobile phase:
  A: 0.1% aqueous TFA
  B: 0.1% TFA in acetonitrile gradient from 80% B to 99% B in 20 minutes
Retention time: about 23 minutes 7.2 Preparation of Fragment Fmoc-AA(9-15)-OH (Fragment 5b)
Structure
  Fmoc-Ile-Glu(tBu)-Glu(tBu)-Ser(tBu)-Gln(trt)-Asn(trt)-Gln(trt)-OH (SEQ ID NO:6)

|  | $C_{117}H_{129}N_{10}O_{18}$ MW 1963.39 | | | | |
|---|---|---|---|---|---|
| Materials: | MW | eq | mmoles | grams | mL |
| Fmoc-Gln (trt) -2-chlorotrityl resin | — | 1.0 | 12.0 | 20.0 | — |
| Fmoc-amino acid* | — | 1.5 | 18.0 | — | — |
| 1-Hydroxybenzotriazole (HOBT) hydrate* | 153.15 | 1.5 | 18.0 | 2.8 | — |
| O-Benzotriazol-1-yl-N,N,N',N'-tetramethyluronium hexafluorophosphate (HBTU)* | 379.25 | 1.5 | 18.0 | 6.8 | — |
| Diisopropylethylamine (DIEA)* | 129.25 | 1.5 | 18.0 | 2.3 | 3.1 |
| N-methyl-2-pyrrolidinone (NMP)* | — | — | — | — | 150 |
| Methylene chloride (DCM)* | — | — | — | — | 50 |
| 20% piperidine/NMP* | — | — | — | — | 2 × 200 |
| NMP for rinsing* | — | — | — | — | 200 (per wash) |
| DCM for cleavage | — | — | — | — | 160 |
| Acetic acid (HOAc) | — | — | — | — | 20 |
| Trifluoroethanol | — | — | — | — | 20 |
| Heptane | — | — | — | — | 250 + 250 + 100 |
| Methyl t-butyl ether | — | — | — | — | 100 |
| Isopropanol | — | — | — | — | 60 |
| Water | — | — | — | — | 60 + 50 |

*per coupling cycle
Theoretical Yield: 23.6 g
Expected Yield: 89–95%
Actual Yield: 21.1 g Procedure:
The procedure used in the Example presented in Section 7.1, above was repeated using 20.0 g Fmoc-Gln(trt)-2-chlorotrityl resin, and Fmoc-protected amino acids Asn(trt), Gln(trt), Ser(tBu), Glu(tBu), Glu(tBu) and Ile.

Following the final coupling reaction, the resin was washed 4×200 mL (10 vol) of NMP, then with 4×200 mL (10 vol) of DCM.

The peptide was cleaved from the resin using 200 mL of 8:1:1 DCM:TFE:HOAc for 2 hours, followed by 2×100 mL washes of DCM. The combined eluants were concentrated under vacuum to a volume of ~100 mL, then reconstituted with 250 mL of heptane while the concentration was continued to remove residual DCM to a final volume of ~250 mL. The heptane layer was separated from the biphasic mixture which formed. The product was precipitated with the addition of 250 mL of heptane and 100 mL of MTBE, then triturated overnight at room temperature to give material of desired consistency. The solids were collected by vacuum filtration and washed with about 100 mL of heptane. The product was reworked to remove residual acetic acid. The filtered solids were dissolved in 60 mL of isopropanol at 50° C. The solution was chilled in an ice bath to 0–5° C., then 60 mL of water was added at a rapid dropwise rate. The product slurry was triturated with stirring for ~1 hour in the ice bath. The solids were isolated by vacuum filtration and washed with ~50 mL of water. The product was air dried to give 21.1 g (90%) of Fmoc-AA(9-15)-OH of 95% HPLC purity.

Column: Phenomenox Jupiter C18
Flow rate: 1 mL/min
Detection: UV at 260 nm
Mobile phase:
  A: 0.1% aqueous TFA
  B: 0.1% TFA in acetonitrile gradient from 80% B to 99% B in 20 minutes
Retention time: ~23 minutes 7.3 Preparation of Fragment Fmoc-AA(1-16)-OH (Fragment 3d)
Structure:
  Fmoc-Tyr(tBu)-Thr(tBu)-Ser(tBu)-Leu-Ile-His(trt)-Ser(tBu)-Leu-Ile-Glu(tBu)-Glu(tBu)-Ser(tBu)Gln(trt)-Asn(trt)-Gln(trt)-Gln-OH (SEQ ID NO:4)

|  | $C_{199}H_{245}N_{22}O_{32}$ MW 3457.30 | | | | |
|---|---|---|---|---|---|
| Materials: | MW | eq | mmoles | grams | mL |
| Fmoc-Gln-2-chlorotrityl resin | — | 1.0 | 24.1 | 32.5 | — |
| Fmoc-amino acid* | — | 1.5 | 36.2 | — | — |
| 1-Hydroxybenzotriazole (HOBT) hydrate* | 153.15 | 1.5 | 36.2 | 5.5 | — |

-continued

|  | $C_{199}H_{245}N_{22}O_{32}$ MW 3457.30 | | | | |
|---|---|---|---|---|---|
| Materials: | MW | eq | mmoles | grams | mL |
| O-Benzotriazol-1-yl-N,N,N',N'-tetramethyluronium hexafluorophosphate (HBTU)* | 379.25 | 1.5 | 36.2 | 13.7 | — |
| Diisopropylethylamine (DIEA)* | 129.25 | 1.5 | 36.2 | 4.7 | 6.3 |
| N-methyl-2-pyrrolidinone (NMP)* | — | — | — | — | 200 |
| Methylene chloride (DCM)* | — | — | — | — | 75 |
| 20% piperidine/NMP* | — | — | — | — | 2 × 250 |
| NMP for rinsing* | — | — | — | — | 250 (per wash) |
| 1% Trifluoroacetic acid/DCM | — | — | — | — | 4 × 50 |
| Pyridine | 79.10 | — | — | — | 4 × 0.5 |
| Heptane | — | — | — | — | 150 + 50 |
| Methanol | — | — | — | — | 50 |
| Water | — | — | — | — | 50 + 25 |

*per coupling cycle
Theoretical Yield: 48.9 g
Expected Yield: 85–90%

Procedure:

The procedure used in the Example presented in Section 7.1, above, was repeated using 32.5 g Fmoc-Gln-2-chlorotrityl resin and the required Fmoc-protected amino acids. The reaction was run as described in the Example presented in Section 6.1, above, except slightly different volumes of solvents were used as indicated in the Materials section above.

Following the final coupling reaction, the resin was washed 4×250 mL (8 vol) of NMP, then with 4×250 mL (8 vol) of DCM. The resin was dried under a nitrogen purge to give 97.4 g of bound peptide.

On 17.7-g scale, the resin-bound peptide was cleaved from the resin using 2×190 mL of 1% TFA in DCM for 1–2 minutes, followed by 1×120 mL with DCM. The cleavage fractions were collected onto pyridine (1:1 volume ratio to TFA). The fractions and wash were combined and concentrated under vacuum to a volume of ~50 mL, then reconstituted with 200 mL of methanol. The concentration was continued to remove residual DCM to a final volume of ~50 mL. The product was precipitated with the addition of 250 mL of water and stirred at room temperature for ~30 minutes. The solids were collected by vacuum filtration and washed with ~50 mL of water. The product was air dried to give 12.8 g (84%). The product was reworked to remove pyridinium salts. The filtered solids were dissolved in 150 mL of methanol at room temperature. Addition of 200 mL of water at room temperature precipitated the product. The product was isolated by vacuum filtration and washed with about 50 mL of water. The material was air dried to give 12.8 g (84%) of Fmoc-AA(1-16)-OH.

Column: Phenomenox Jupiter C18

Flow rate: 1 mL/min

Detection: UV at 260 nm

Mobile phase:
  A: 0.1% aqueous TFA
  B: 0.1% TFA in acetonitrile gradient from 75% B to 99% B in 20 minutes Retention time: ~25 minutes 7.4 Preparation of Fragment Ac-AA(1-16)-OH (Fragment 3c)

Structure:

Ac-Tyr(tBu)-Thr(tBu)-Ser(tBu)-Leu-Ile-His(trt)-Ser(tBu)-Leu-Ile-Glu(tBu)-Glu(tBu)-Ser(tBu)-Gln(trt)-Asn(trt)-Gln(trt)-Gln-OH (SEQ ID NO:4)

|  | $C_{186}H_{237}N22O_{31}$ MW 3274.76 | | | | |
|---|---|---|---|---|---|
| Materials: | MW | eq | mmoles | grams | mL |
| Fmoc-Gln-2-chlorotrityl resin | — | 1.0 | 24.1 | 32.5 | — |
| Fmoc-amino acid* | — | 1.5 | 36.2 | — | — |
| 1-Hydroxybenzotriazole (HOBT) hydrate* | 153.15 | 1.5 | 36.2 | 5.5 | — |
| O-Benzotriazol-1-yl-N,N,N',N'-tetramethyluronium hexafluorophosphate (HBTU)* | 379.25 | 1.5 | 36.2 | 13.7 | — |
| Diisopropylethylamine (DIEA)* | 129.25 | 1.5 | 36.2 | 4.7 | 6.3 |
| N-methyl-2-pyrrolidinone (NMP)* | — | — | — | — | 200 |
| Methylene chloride (DCM)* | — | — | — | — | 75 |
| 20% piperidine/NMP* | — | — | — | — | 2 × 250 |
| NMP for rinsing* | — | — | — | — | 250 (per wash) |
| 1% Trifluoroacetic acid/DCM | — | — | — | — | 4 × 50 |
| Pyridine | 79.10 | — | — | — | 4 × 0.5 |
| Heptane | — | — | — | — | 150 + 50 |

-continued $C_{186}H_{237}N22O_{31}$
MW 3274.76

| Materials: | MW | eq | mmoles | grams | mL |
|---|---|---|---|---|---|
| Methanol | — | — | — | — | 50 |
| Water | — | — | — | — | 50 + 25 |

*per coupling cycle
Theoretical Yield: 48.9 g
Expected Yield: 85–90%

Procedure:

The procedure used in the Example presented in Section 7.1, above, was repeated using 32.5 g Fmoc-Gln-2-chlorotrityl resin and the required Fmoc-protected amino acids, and the solvent volumes indicated in the materials section above.

Following the final coupling reaction, the resin was washed 4×250 mL (8 vol) of NMP, then with 4×250 mL (8 vol) of DCM. The resin was dried under a nitrogen purge to give 97.4 g of bound peptide.

On 10-g scale, the resin-bound peptide was acetylated with acetic anhydride and pyridine (5 eq each) in 100 mL of 3:1 NMP:DCM for 30 minutes, then washed with 2×25 mL DCM. The peptide was cleaved from the resin using 3×50 mL of 1% TFA in DCM, followed by 2×50 mL washes of DCM. The cleavage fractions were collected onto pyridine (1:1 volume ratio to TFA). The fractions and wash were combined and concentrated under vacuum to a volume of about 100 mL, then reconstituted with 3×50 mL of heptane added portionwise while the concentration was continued to remove residual DCM to a final volume of ~150 mL. The product precipitated initially with a somewhat tacky consistency but triturated with stirring for ~30 minutes in an ice bath at 0–5° to a filterable solid. The solids were collected by vacuum filtration and washed with ~50 mL of heptane. The product was reworked to remove pyridinium salts. The filtered solids were dissolved in 50 mL of methanol at room temperature. The solution was chilled in an ice bath to 0–5° C., then 50 mL of water was added at a rapid dropwise rate. The material initially precipitated as a tacky solid which triturated to filterable consistency with stirring for ~1 hour in the ice bath. The product was isolated by vacuum filtration and washed with ~25 mL of water. The product was air dried to give 7.0 g (90%) of AcAA(1-16)-OH. The product was subsequently reworked as described above to give 6.2 g (89% recovery) of material of 96% HPLC purity.

Column: Zorbax LP C8, 100 Å, 20$\mu$

Flow rate: 1 mL/min

Detection: UV at 220 nm

Mobile phase:
  A: 0.1% aqueous TFA
  B: 1:1 ACN:IPA with 0.05% TFA gradient from 80% B to 99% B in 20 minutes Retention time: ~15 minutes 7.5 Preparation of Fragment Fmoc-AA(17-26)-OH (Fragment 10b)

Structure:

Fmoc-Glu(tBu)-Lys(Boc)-Asn(trt)-Glu(tBu)-Gln(trt)-Glu(tBu)-Leu-Leu-Glu(tBu)-Leu-OH (SEQ ID NO:11)

$C_{127}N_{167}N_{13}O_{25}$
MW 2275.82

| Materials: | MW | eq | mmoles | grams | mL |
|---|---|---|---|---|---|
| Fmoc-Leu-2-chlorotrityl resin | — | 1.0 | 19.5 | 25.0 | — |
| Fmoc-amino acid* | — | 1.5 | 30.0 | — | — |
| 1-Hydroxybenzotriazole( HOBT) hydrate* | 153.15 | 1.5 | 30.0 | 4.6 | — |
| O-Benzotriazol-1-yl-N,N,N',N'-tetramethyluronium hexafluorophosphate (HBTU)* | 379.25 | 1.5 | 30.0 | 11.4 | — |
| Diisopropylethylamine (DIEA)* | 129.25 | 1.5 | 30.0 | 3.9 | 5.2 |
| N-methyl-2-pyrrolidinone (NMP)* | — | — | — | — | 200 |
| Methylene chloride (DCM)* | — | — | — | — | 75 |
| 20% piperidine/NMP* | — | — | — | — | 2 × 250 |
| NMP for rinsing* | — | — | — | — | 250 (per wash) |
| 1% Trifluoroacetic acid/DCM | — | — | — | — | 3 × 400 |
| Pyridine | 79.10 | — | 150 | — | 3 × 4 |
| Ethanol, denatured | — | — | — | — | 300 |
| Water | — | — | — | — | 300 |

*per coupling cycle
Theoretical Yield: 44.4 g
Expected Yield: 90–105%
Actual Yield: 46.9 (105%)

Procedure:

The procedure used in the Example presented in Section 7.1., above, was repeated using 25.0 g Fmoc-Leu-2-chlorotrityl resin, the required Fmoc-protected amino acids, and the solvent volumes indicated in the materials section above.

Following the final coupling reaction, the resin was washed 4×250 mL (10 vol) of NMP, then with 4×250 mL (10 vol) of DCM.

The peptide was cleaved from the resin using 3×400 mL (~15 vol) of 1% TFA in DCM, followed by 1×200 mL (7.5 vol) of DCM. The cleavage fractions were collected onto pyridine (1:1 volume ratio to TFA), then the fractions and wash were analyzed for product content. The fractions containing product were combined and concentrated under vacuum to a volume of ~100 mL, then reconstituted with 300 mL of ethanol. The concentration was continued to remove residual DCM to a final volume of ~250 mL. To the stirred solution was added 300 mL of water to precipitate the product. The solids were collected by vacuum filtration and washed with ~50 ML of water. The product was air dried to give 46.4 g(105%) of Fmoc-AA(17-26)-OH of 97% HPLC purity.

Column: Phenomenox Jupiter C18

Flow rate: 1 mL/min

Detection: UV at 260 nm

Mobile phase:
  A: 0.1% aqueous TFA
  B: 0.1% TFA in acetonitrile gradient from 75% B to 99% B in 20 minutes Retention time: ~25 minutes 7.6 Preparation of Fragment Fmoc-AA(27-35)-OH (Fragment 16b)
Structure:
  Fmoc-Asp(tBu)-Lys(Boc)-Trp(Boc)-Ala-Ser(tBu)-Leu-Trp(Boc)-Asn(trt)-Trp(Boc)-OH (SEQ ID NO:17)

for 2 hrs. The resin was drained and washed with 2×250 mL of DCM. The cleavage solution and washes were combined and concentrated to a volume of ~50 mL, then reconstituted with 250 mL of ethanol. The solution was chilled with stirring in an ice bath to 0–5° C. To the stirred solution was added 125 mL of water to precipitate the product. The solids were collected by vacuum filtration and washed with ~50 mL of water. The product was air dried to give 32.0 g(65.4%) of Fmoc-AA(27-35)-OH of 95% HPLC purity.

The resin was treated with 2×250 mL of a 1% solution of TFA in DCM followed by a wash with 100 mL of DCM. The cleavage fractions were collected onto pyridine in a 1:1 volume ratio with TFA. The combined eluants and wash were concentrated to ~50 mL volume. To the solution was added 100 mL ethanol, then 150 mL of water. The product slurry was vacuum filtered yielding a second crop of 10.7 g (21.9%)(95% HPLC purity) to give a combined yield of 87.3%. The 1% TFA/DCM cleavage is preferred due to its greater effectiveness and lower volumes.

Column: Phenomenox Jupiter C5, 300 Å, 5μ

Flow rate: 0.75 mL/min

Detection: UV at 260 nm

Mobile phase:
  A: 0.05% aqueous TFA
  B: 0.1% TFA in 1:1 IPA:MeOH gradient from 70% B to 97% B in 10 minutes Retention time: ~25 minutes

8. EXAMPLE
SOLUTION PHASE SYNTHESIS OF PEPTIDE FRAGMENTS

Presented below, in Sections 8.1–8.11, are examples of the solution phase synthesis of peptide intermediates as listed in Tables 1, 2, and/or 3.

|  | $C_{121}H_{148}N_{14}O_{24}$ MW 2182.61 | | | | |
|---|---|---|---|---|---|
| Materials: | MW | eq | mmoles | grams | mL |
| Fmoc-Trp (Boc) -2-chlorotrityl resin | — | 1.0 | 22.4 | 33.0 | — |
| Fmoc-amino acid* | — | 1.5 | 33.6 | — | — |
| 1-Hydroxybenzotriazole (HOBT) hydrate* | 153.15 | 1.5 | 33.6 | 5.1 | — |
| O-Benzotriazol-1-yl-N,N,N',N'-tetramethyluronium hexafluorophosphate (HBTU)* | 379.25 | 1.5 | 33.6 | 12.7 | — |
| Diisopropylethylamine (DIEA)* | 129.25 | 1.5 | 33.6 | 4.3 | 5.8 |
| N-methyl-2-pyrrolidinone (NMP)* | — | — | — | — | 225 |
| Methylene chloride (DCM)* | — | — | — | — | 75 |
| 20% piperidine/NMP* | — | — | — | — | 2 × 250 |
| NMP for rinsing* | — | — | — | — | 250 (per wash) |
| Trifluoronthanol | — | — | — | — | 30 |
| DCM for cleavage | — | — | — | — | 240 |
| Ethanol, denatured | — | — | — | — | 300, 150 |
| Water | — | — | — | — | 300, 150 |
| 1% Trifluoroaetic acid (TFA) in DCM | — | — | — | — | 2 × 250 |
| Pyridine | 79.10 | — | — | — | 2 × 2.5 |

*per coupling cycle
Theoretiaal Yield: 48.9 g
Expected Yield: 85–90%

Procedure:
The procedure used in the Example presented in Section 7.1, above, was repeated using 33.0 g Fmoc-Trp(Boc)-2-chlorotrityl resin, the required Fmoc-protected amino acids, and the materials indicated in the Materials section above.

Following the final coupling reaction, the resin was washed 4×250 mL (7.5 vol) of NMP, then with 4×250 mL (7.5 vol) of DCM.

The peptide was cleaved from the resin by treatment with 300 mL (~10 vol) of a solution of 8:1:1 DCM:TFE:HOAc 8.1 Preparation of Fragment Fmoc-AA9-16OPNB by Coupling of Para Nitrobenzylester (OPNB) of Glutamine to Fmoc-AA9-15OH Structure:

Fmoc-Ile-Glu(OtBu)-Glu(OtBu)-Ser(tBu)-Gln(trt)-Asn(trt)-Gln(trt)-Gln-OPNB (SEQ ID NO:7)

|  | $C_{129}H_{141}N_{13}O_{22}$ MW 2227.65 | | | | |
|---|---|---|---|---|---|
| Materials: | MW | eq | mmoles | grams | mL |
| FmocAA9-15OH | 1963.39 | 1 | 9.7 | 19 | — |
| HBrGlnOPNB (BaChem, #509709) | 362.19 | 1.1 | 10.6 | 3.85 | — |
| HOAT | 136 | 1.1 | 10.6 | 1.45 | — |
| HBTU | 379.25 | 1.1 | 10.6 | 4.04 | — |
| EtPr$_2$N (d = 0.755) | 129.25 | 2.1 | 20.3 | 2.62 | 3.48 |
| NMP | — | — | — | — | 200 |
| 0.5 N HCl | — | — | — | — | 250 |
| ethyl acetate | — | — | — | — | 250 |
| hexane | — | — | — | — | 250 |

Theoretical Yield: 21.5 g
Expected Yield: 90–105%

Procedure:

FmocAA9-15OH (as synthesized in Section 7.2, above), HBrGlnOPNB (SEQ ID NO:4) HOAT and EtPr$_2$N were combined in a 1 L round bottom flask containing a magnetic stir bar and NMP (200 mL) was added. The resulting solution was placed under a nitrogen atmosphere and cooled to 0–5° C. with stirring. To the cool solution was added HBTU. The solution was stirred for 15 minutes at 0–5° C., the ice bath was removed and stirring was continued for 2.5 hours (note 1).

The reaction mixture was cooled to 0–5° C., and 0.5N aqueous HCl (250 mL) was added to precipitate the protected peptide. The solids were collected by vacuum filtration and dried in the filter flask to yield 24 g of crude FmocAA9-16OPNB. The solid was dissolved in ethyl acetate (250 mL), dried over magnesium sulfate (10 g), filtered and concentrated to a volume of 100 mL. The solution was cooled to 0–5° C. and hexane (250 mL) was added to precipitate the peptide. The solid was collected by vacuum filtration and dried providing 21.5 g of FmocAA9-16OPNB in 100% yield and 91–94% HPLC purity (note 2).

Notes:
1 In process control is thin layer chromatography (TLC).
   90/10 chloroform/ethanol
   UV, Iodine detection
   Rt FmocAA9-15OH 0.46
   Rt FmocAA9-16OPNB 0.57
2 Phenomenex Jupiter, C5, 5μ, 300 A
   0.75 ml/min, 260 nm
   A H$_2$O/0.05% TFA
   B 50% IPA/MeOH/0.05% TFA
   70–97% B over 10 min, 97% B for 8 min.
   Retention time: 13.3 minutes 8.2 Preparation of Fragment HCl HAA9-16OPNB
Structure:
   HCl H-Ile-Glu(OtBu)-Glu(OtBu)-Ser(tBu)-Gln(trt)-Asn(trt)-Gln(trt)-Gln-OPNB (SEQ ID NO:7)

|  | $C_{144}H_{131}ClN_{13}O_{20}$ MW 2041.02 | | | | |
|---|---|---|---|---|---|
| Materials: | MW | eq | mmoles | grams | mL |
| FmocAA9-16OPNB | 2227.65 | 1 | 9.43 | 21 | — |
| Piperidine | — | — | — | — | 10 |
| THF | — | — | — | — | 190 |
| Methyl tertbutyl ether (MTBE) | — | — | — | — | 250 |
| Hexane | — | — | — | — | 350 |

|  | $C_{144}H_{131}ClN_{13}O_{20}$ MW 2041.02 | | | | |
|---|---|---|---|---|---|
| Materials: | MW | eq | mmoles | grams | mL |
| Methanol | — | — | — | — | 150 |
| 0.5 N HCl | — | — | — | — | 100 |
| 2-propanol | — | — | — | — | 50 |

Theoretical Yield: 19.2 g
Expected Yield: 85–105%

Procedure:

A 1 L round bottom flask containing a magnetic stir bar was charged with FmocAA9-16OPNB (as synthesized in Section 8.1, above) and 20:1 tetrahyrofuran/piperidine. The resulting solution was stirred under an atmosphere of nitrogen at room temperature for 60 minutes (note 1). Hexane (350 mL) was added to precipitate the peptide. The solvent was decanted from the sticky solid. The solid was triturated with MTBE (200 mL) at room temperature for 18 hours. The solid was collected by vacuum filtration and dried to give 18.9 g of HAA9-16OPNB (note 2).

The solid was dissolved in methanol (150 ml), cooled to 0–5° C. with stirring. 0.5N aqueous hydrochloric acid (100 ml) was added to precipitate the peptide. The solids were collected by vacuum filtration, washed with water (50 mL) then 2-propanol (50 mL) and dried to give 17.7 g of HCl HAA9-16OPBN in 92% yield and an HPLC purity of 92 A % (note 3).

Notes:
1 In process control, HPLC
   Phenomenex Jupiter, C5, 5μ, 300 A
   0.75 ml/min, 260 nm
   A H$_2$O/0.05% TFA
   B 50% IPA/MeOH/0.05% TFA
   70–97% B over 10 min, 97% B for 8 min.
   Retention time: FmocAA9-16OPNB, 13.3 minutes; HAA9-16OPNB, 10.7 minutes
2 HAA9-16OPNB isolated at this point contains trace amounts of piperidine and the benzylfulvene piperidine adduct. Both are removed before coupling with RAA1-8OH.
3 Phenomenex Jupiter, C5, 5μ, 300 A
   0.75 ml/min, 260 nm
   A H$_2$O/0.05% TFA
   B 50% IPA/MeOH/0.05% TFA
   80–100% B over 10 min, 100% B for 5 min.
   Retention time: HAA9-16OPNB, 7.2 minutes TLC conditions: 90/10 dichloromethane/ethanol UV, iodine detection Rf: HAA9-16OPNB, 0.64

8.3 Preparation of Fragment AcAA1-16OPNB by Solution-Phase Coupling of Fragments AcAA1-8OH and HAA9-16OPNB (SEQ ID NO:4)

Structure:

Ac-Tyr(tBu)-Thr(tBu)-Ser(tBu)-Leu-Ile-His(trt)-Ser(tBu)-Leu-Ile-Glu(OtBu)-Glu(OtBu)-Ser(tBu)-Gln(trt)-Asn(trt)-Gln(trt)-Gln-OPNB $C_{194}H_{246}N_{23}O_{34}$
MW 3427.43

| Materials: | MW | eq | mmoles | grams | mL |
|---|---|---|---|---|---|
| AcAA1-8OH | 1440.86 | 1.3 | 0.13 | 0.186 | — |
| HCl HAA9-16OPNB | 2041.02 | 1 | 0.10 | 0.204 | — |
| HBTU | 379.25 | 1.1 | 0.11 | 0.042 | — |
| HOAT | 136.1 | 1.1 | 0.11 | 0.015 | — |
| EtPr$_2$N | 129.25 | 2.1 | 0.21 | 0.027 | 0.036 |
| DMF | — | — | — | — | 4.5 |
| DMSO | — | — | — | — | 0.5 |
| water | — | — | — | — | 7 |
| MTBE | — | — | — | — | 3.5 |

Theoretical Yield: 0.38
Expected Yield: 85–105%

Procedure:

A 25 mL round bottom flask containing a magnetic stir bar was charged with AA1-8OH (as synthesized in Section 7.1, above), HCl HAA9-16OPNB (as synthesized in Section 8.2, above) and HOAT. The solids were dissolved in 9:1 DMF:DMSO (5 mL) containing EtPr$_2$N, then cooled to 0–5° C. under an atmosphere of nitrogen (note 1). To the cool solution was added HBTU. The reaction mixture was stirred at 0–5° C. for 15 minutes, then warmed to room temperature and stirred an additional 60 minutes (note 2). The peptide was precipitated from the solution by addition of water (7 mL). The solids were collected by vacuum filtration, washed with water (10 mL) and dried to give 0.36 g of crude AcAA1-16OPNB. The solid was triturated with MTBE (3.5 mL) for 1.5 hours at room temperature, collected by vacuum filtration and dried to give 0.335 g of AcAA-16OPNB in 88% yield and 82 A % HPLC purity (note 3).

Notes:

1 It is important that all the solids are in solution before cooling to 0–5° C. and adding HBTU.

2 In process control, TLC, HPLC
  Phenomenex Jupiter, C5, 5μ, 300 A
  0.75 ml/min, 260 nm
  A H$_2$O/0.05% TFA
  B 50% IPA/MeOH/0.05% TFA
  80–100% B over 10 min, 100% B for 5 min.
  Retention time: HAA9-16OPNB, 7.2 minutes (Ac1-8OH has no absorbance at 260 nm).
  Retention time: AcAA1-16OPNB, 12.45
  TLC conditions
    90/10 chloroform/ethanol UV, iodine detection
    Rf: HAA9-16OPNB, 0.64
    Rf: Ac1-8OH, 0.35
    Rf: Ac1-16OH, 0.48

3 Phenomenex Jupiter, C5, 5μ, 300 A
  0.75 ml/min, 260 nm
  A H$_2$O/0.05% TFA
  B 50% IPA/MeOH/0.05% TFA
  70–97% B over 10 min, 97% B for 8 min
  Retention time: Ac1-16OPNB, 16.4.

8.4 Preparation of Fragment FmocAA1-16OPNB by Solution-Phase Coupling of Fragments FmocAA1-8OH and HCl HAA9-16OPNB Structure:

Fmoc-Tyr(tBu)-Thr(tBu)-Ser(tBu)-Leu-Ile-His(trt)-Ser(tBu)-Leu-Ile-Glu(OtBu)-Glu(OtBu)-Ser(tBu)-Gln(trt)-Asn(trt)-Gln(trt)-Gln-OPNB (SEQ ID NO:4)

$C_{207}H_{253}N_{23}O_{34}$
MW 3607.49

| Materials: | MW | eq | mmoles | grams | mL |
|---|---|---|---|---|---|
| FmocAA1-8OH | 1620.92 | 1 | 7.84 | 12.7 | — |
| HCl HAA9-16OPNB | 2041.02 | 1 | 7.84 | 16.0 | — |
| HBTU | 379.25 | 1.2 | 9.42 | 3.57 | — |
| HOAT | 136.1 | 1.2 | 9.42 | 1.28 | — |
| EtPr$_2$N (d = 0.755) | 129.25 | 2.5 | 19.6 | 2.55 | 3.36 |
| DMF | — | — | — | — | 250 |
| 10% sodium chloride/water (wt/vol) | — | — | — | — | 450 |
| methanol | — | — | — | — | 200 |
| water | — | — | — | — | 100 |

Theoretical Yield: 28.3 g
Expected Yield: 85–100%

Procedure:

A 1 L round bottom flask containing a magnetic stir bar was charged with FmocAA1-8OH (as synthesized in Section 7.1, above), HCl HAA9-16OPNB (as synthesized in Section 8.2, above), HOAT and DMF (250 mL). To the solution was added EtPr$_2$N. The solution was cooled to 0–5° C. and HBTU was added. The reaction mixture was stirred at 0–5° C. for 15 minutes, then warmed to room temperature and stirred an additional 70 minutes (note 1). The reaction mixture was cooled to 0–5° C. and 10% sodium chloride/water (200 mL) was added to precipitate the peptide. The solids were collected by vacuum filtration, washed with water (50 mL) and dried to give 27 g of crude FmocAA1-16OPNB. The solid was dissolved in methanol (200mL) and added to a stirred solution of sodium chloride in water (10% wt/vol, 300 mL). The solids were collected by vacuum filtration, washed with water (50 mL) and dried to give 26 g of FmocAA1-16OPNB in 92% yield and 90 A % purity by HPLC (note 1).

Notes:

1 In process control, HPLC
  Phenomenex Jupiter, C5, 5μ, 300 A
  0.75 ml/min, 260 nm
  A H$_2$O/0.05% TFA
  B 50% IPA/MeOH/0.05% TFA
  80–100% B over 10 min, 100% B for 5 min.
  Retention time: HAA9-16OPNB, 7.2 minutes, FmocAA1-8OH, 7.9 minutes
  Retention time: FmocAA1-16OPNB, 14.5 minutes

8.5 Preparation of Fragment H-AA1-16OPNB

Structure:

H-Tyr(tBu)-Thr(tBu)-Ser(tBu)-Leu-Ile-His(trt)-Ser(tBu)-Leu-Ile-Glu(tBu)-Glu(tBu)-Ser(tBu)-Gln(trt)-Asn(trt)-Gln(trt)-Gln-OPNB

| | $C_{192}H_{243}N_{23}O_{32}$ | | | | |
|---|---|---|---|---|---|
| | MW 3384.41 | | | | |
| Materials: | MW | eq | mmoles | grams | mL |
| FmocAA1-16OPNB | 3607.49 | 1 | 0.28 | 1.0 | — |
| piperidine | — | — | — | — | 0.6 |
| dichloromethane | — | — | — | — | 11.4 |
| hexane | — | — | — | — | 45 |

Theoretical Yield: 0.94 g
Expected Yield: 90–105%

Procedure:
A 50 mL round bottom flask containing a magnetic stir bar was charged with FmocAA1-16OPNB (as synthesized in Section 8.4, above), dichloromethane (11.4 mL) and piperidine (0.6 mL). The solution was stirred at room temperature under an atmosphere of nitrogen for 90 minutes (note 1). Hexane (45 mL) was added to the reaction mixture and the solvent volume was reduced to 25 mL by vacuum distillation. The resulting solids were collected by vacuum filtration and dried to give 0.96 g of HAA1-16OPNB in 102% yield. HPLC analysis of the solid indicated 72 A % HAA1-16OPNB and 18 A % fulvene and piperidine-fulvene adduct.

Notes:
1 Phenomenex Jupiter, C5, 5μ, 300 A
  0.8 ml/min, 260 nm
  A $H_2O$/0–05% TFA
  B 50% IPA/MeOH/0.05% TFA
  80–100% B over 10 min, 100% B for 5 min
  Retention time FmocAA1-16OPNB, 14.1 min
  Retention time HAA1-16OPNB, 11.6 min
  Retention time fulvene and piperdine-fulvene adduct, 5.5 and 4.8 min.

8.6 Preparation of Fragment Ac-AA1-16OPNB by Acetylation of N-terminus of HAA1-16OPNB
Structure:
Ac-Tyr(tBu)-Thr(tBu)-Ser(tBu)-Leu-Ile-His(trt)-Ser(tBu)-Leu-Ile-Glu(tBu)-Glu(tBu)-Ser(tBu)-Gln(trt)-Asn(trt)-Gln(trt)-Gln-OPNB (SEQ ID NO:4)

| | $C_{194}H_{246}N_{23}O_{34}$ | | | | |
|---|---|---|---|---|---|
| | MW 3427.43 | | | | |
| Materials: | MW | eq | mmoles | grams | mL |
| HAA1-16OPNB | 3384.41 | 1 | 0.28 | 0.95 | — |
| acetic anhydride (d = 1.08) | 102.09 | 3 | 0.84 | 0.086 | 0.080 |
| pyridine (d = 0.978) | 79.1 | 3 | 0.84 | 0.67 | 0.068 |
| DMF | — | — | — | — | 10 |
| water | — | — | — | — | 30 |
| MTBE | — | — | — | — | 10 |
| hexane | — | — | — | — | 10 |

Theoretical Yield: 0.96 g
Expected Yield: 80–100%

Procedure:
A 50 mL round bottom flask containing a magnetic stir bar was charged with HAA1-16OPNB (as synthesized in Section 8.5, above), DMF (10 mL), acetic anhydride and pyridine. The reaction mixture was stirred at room temperature under an atmosphere of nitrogen for 60 min (note 1). Water (20 mL) was added to precipitate the peptide. The solids were collected by vacuum filtration, washed with water (10 mL) and dried to give 0.87 g of AcAA1-16OPNB. To remove residual fulvene and piperidine-fulvene adduct, the solid was triturated with 1:1 MTBE/hexane (20 mL) for 4.5 hours at room temperature. The solids were collected by vacuum filtration and dried to give 0.82 g of AcAA1-16OPNB in 85% yield and >90 A % purity by HPLC (note 1).

Notes:
1 In process control, HPLC
  Phenomenex Jupiter, C5, 5μ, 300 A
  0.8 ml/min, 260 nm
  A $H_2O$/0.05% TFA
  B 50% IPA/MeOH/0.05% TFA
  80–100% B over 10 min, 100% B for 15 min
  Retention time HAA1-16OPNB, 11.6 min
  Retention time AcAA1-16OPNB, 12.1 min
  TLC, 10% ethanol in dichloromethane
  UV, Iodine detection
  Rf AcAA1-16OPNB, 0.69

8.7 Preparation of Fragment AcAA1-16OH by Selective Removal of a Paranitrobenzyl Protecting Group From AcAA1-16OPNB in the Presence of His(trt).
Structure:
Ac-Tyr(tBu)-Thr(tBu)-Ser(tBu)-Leu-Ile-His(trt)-Ser(tBu)-Leu-Ile-Glu(OtBu)-Glu(OtBu)-Ser(tBu)-Gln(trt)-Asn(trt)-Gln(trt)-Gln-OH (SEQ ID NO:4)

| | $C_{187}H_{241}N_{22}O_{32}$ | | | | |
|---|---|---|---|---|---|
| | MW 3276.4 | | | | |
| Materials: | MW | eq | mmoles | grams | mL |
| AcAA1-16OPNB | 3424.86 | 1 | 0.23 | 0.80 | — |
| 10% Pd/C, Degussa, 50% water | — | — | — | 0.30 | — |
| ammonium formate | 63.06 | 15 | 3.5 | 0.22 | — |
| DMF | — | — | — | — | 15 |
| Water | — | — | — | — | 120 |
| Ethyl acetate | — | — | — | — | 100 |
| Hexane | — | — | — | — | 44 |
| methanol | — | — | — | — | 10 |
| saturated aq.NaCl | — | — | — | — | 5 |
| MTBE | — | — | — | — | 4 |

Theoretical Yield: 0.76 g
Expected Yield: 70–85%

Procedure:
A 25 mL round bottom flask containing a magnetic stir bar was charged with AcAA1-16OPNB (as synthesized in Section 8.6, above) sand DMF (10 ml). To this solution was added a solution of ammonium formate in water (0.5 mL), then wet palladium on carbon (Degussa, 10%, 50% water). The slurry was stirred under an atmosphere of nitrogen at room temperature for 120 minutes (note 1). The slurry was filtered through a tightly packed bed of celite into 90 mL of water. The filter cake was washed with DMF (5 mL). The aqueous suspension was washed with ethyl acetate (100 mL). The ethyl acetate was then concentrated to a volume of 20 mL (note 2). Hexane (40 mL) was added to complete the precipitation and the solvent was decanted from the solids. The solids were dissolved in methanol (10 mL) and 4:1 water/saturated aqueous sodium chloride (25 mL) was added to precipitate the peptide. The solids were collected by vacuum filtration, washed with water (10 mL) and dried to give 0.62 g of AcAA1-16OH. The solids were triturated with 50% MTBE/hexane (8 mL) at room temperature for 15 hours, collected and dried to give 0.59 g of AcAA1-16OH in 77% yield and 90 A % purity by HPLC (note 3).

Notes:
1 In process control, TLC
  80/20 dichloromethane/ethanol
  UV, iodine detection
  Rf: AcAA1-16OPNB, 0.90
  Rf: Ac1-16OH, 69
2 The AcAA1-16OH may begin to precipitate as the solvent volume is reduced.

3 Phenomenex Jupiter, C5, 5μ, 300 A
0.8 mL/min, 260 nm
A H$_2$O/0.05% TFA
B 50% IPA/MeOH/0.05% TFA
80–100% B over 10 minutes, 100% B for 5 minutes
Retention time: AcAA1-16OH, 10.73 minutes.

8.8 Preparation of Fragment FmocAA27-36NH$_2$ by Solution-Phase Coupling of FmocAA27-35OH With HPheNH$_2$ Structure:
Fmoc-Asp(tBu)-Lys(Boc)-Trp(Boc)-Ala-Ser(tBu)-Leu-Trp(Boc)-Asn(trt)-Trp(Boc)-Phe-NH$_2$ (SEQ ID NO:18)

| | $C_{130}H_{159}N_{16}O_{24}$ MW 2329.64 | | | | |
|---|---|---|---|---|---|
| Materials: | MW | eq | mmoles | grams | mL |
| FmocAA27-35OH | 2182.61 | 1 | 18.4 | 40.2 | — |
| HPheNH$_2$ | 162.21 | 1.2 | 22.1 | 3.6 | |
| HBTU | 379.25 | 1.2 | 22.1 | 8.4 | |
| HOAT | 136.1 | 1.2 | 22.1 | 3.0 | |
| EtPr$_2$N (d = 0.755) | 129.25 | 2.1 | 38.7 | 5.0 | 6.6 |
| DMF | | | | | 500 |
| Water | | | | | 600 |

Theoretical Yield 42.8 g
Expected Yield: 90–105%

Procedure:
A 2 L round bottom flask containing a magnetic stir bar was charged with FmocAA27-35OH (as synthesized in Section 7.6, above), HOAT, HpheNH$_2$ and DMF (500 mL). EtPr$_2$N was added and the solution was cooled to 0–5° C. then HBTU was added. The reaction mixture was stirred for 15 minutes at 0–5° C. then warmed to room temperature and stirred an additional 70 minutes (note 1). The solution was cooled to 0–5° C. and water (500 mL) was added to precipitate the peptide. The solids were collected by vacuum filtration, washed with water (100 mL) and dried to give 43 g of FmocAA27-36NH$_2$ in 100% yield and 93 A % purity by HPLC (note 2).

Notes:
1 In process control, TLC
   88/12 dichloromet:hane/methanol
   UV, iodine detection
   Rf: FmocAA27-35OH, 0.49
   Rf: FmocAA27-36NH$_2$, 0.63
2 Phenomenex Jupiter, C18, 5μ, 300 A
   1.0 ml/min, 260 nm
   A H$_2$O/0.1% TFA
   B ACN
   75–99% B over 20 min, 99% B for 5 min.
   Retention time: 29.4 minutes

8.9 Preparation of Fraqment H-AA(27-36)-NH$_2$

Structure:

H-Asp(tBu)-Lys(Boc)-Trp(Boc)-Ala-Ser(tBu)-Leu-Trp(Boc)-Asn(trt)-Trp(Boc)-NH$_2$ (SEQ ID NO:17)

| | $C_{115}H_{148}N_{16}O_{22}$ MW 2106.56 | | | | |
|---|---|---|---|---|---|
| Materials: | MW | eq | mmoles | grams | mL |
| FmocAA(27–36)-NH$_2$ | 2328.8 | 1.0 | 9.3 | 21.7 | — |
| Piperidine | 85.15 | 5.0 | 46.6 | 4.0 | 4.6 |
| Methylene chloride (DCM) | — | — | — | — | 100 |
| Water | — | — | — | — | 2 × 100 |
| Methyl t-butyl ether (MTBE) | — | — | — | — | 100 + 30 |

Theoretical Yield 19.6 g
Expected Yield: 85–95%

Procedure:
To a 250 mL round bottom flask equipped with a magnetic stirrer and nitrogen blanket was charged the Fmoc-fragment synthesized in Section 8.8, above, the methylene chloride (~5 vol), and the piperidine. A solution was obtained and stirred at room temperature for 1.5 hours (Note 1).

The solution was washed with 2×100 mL of water. The layers were separated and the organic layer was concentrated under vacuum to ~½ original volume. MTBE was added portionwise, 2×50 mL, while the concentration was continued to remove DCM to a point of heavy precipitation and a final pot volume of ~150 mL.

The product slurry was stirred and chilled in an ice bath at 0–5° C. for ~1 hour. The solids were isolated by vacuum filtration and washed with 2×15 mL of MTBE. The product was air dried to give 17.6 g (89.6%) of H-AA(27-36)NH$_2$ of 95% HPLC purity (Note 2).

Notes:
1) Reaction completion is monitored by HPLC:
   Column: Phenomenox Jupiter C18; 300 Å; 5μ
   Flow rate: 1 mL/min
   Detection: UV at 260 nm
   Mobile phase:
      A: 0.1% aqueous TFA
      B: 0.1% TFA in acetonitrile gradient from 75% B to 99% B in 20 minutes
   Retention time: ~18 minutes
2) Both of the Fmoc by-products, the dibenzofulvene and its piperidine adduct, are effectively removed in the workup; however, a use-test should be performed before carrying the material forward. If the material fails the use test, the workup procedure is repeated by dissolving the solid in DCM (5 vol), then continuing with the process described above.

8.10 Preparation of Fragment FmocAA17-36NH$_2$ by Solution-phase coupling of FmocAA17-26OH with HAA27-36NH$_2$ Structure:
Fmoc-Glu(OtBu)-Lys(Boc)-Asn(trt)-Glu(OtBu)-Gln(trt)-Glu(OtBu)-Leu-Leu-Glu(OtBu)-Leu-Asp(tBu)-Lys(Boc)-Trp(Boc)-Ala-Ser(tBu)-Leu-Trp(Boc)-Asn(trt)-Trp(Boc)-Phe-NH$_2$ (SEQ ID NO:12)

| | $C_{242}H_{313}N_{29}O_{46}$ MW 4364.38 | | | | |
|---|---|---|---|---|---|
| Materials: | MW | eq | mmoles | grams | mL |
| FmocAA17-26OH | 2275.82 | 1 | 9.5 | 21.6 | |
| HAA27-36NH$_2$ | 2106.56 | 1 | 9.5 | 20 | |
| HOAT | 136.1 | 1.2 | 11.4 | 1.55 | |
| HBTU | 379.25 | 1.2 | 11.4 | 4.33 | |
| EtPr$_2$N (d = 0.755) | 129.25 | 2 | 19.0 | 2.46 | 3.25 |
| DMF | | | | | 400 |
| Water | | | | | 600 |
| 2-propanol | | | | | 1100 |

Theoretical Yield 41.5 g
Expected Yield: 80–85%

Procedure:

A 2 L round bottom flask containing a magnetic stir bar was charged with FmocAA17-26OH (as synthesized in Section 7.5, above), HAA27-36NH$_2$ (as synthesized in Section 8.9, above), HOAT and DMF (400 mL). EtPr$_2$N was added, the stirred solution was cooled to 0–5° C. under an atmosphere of nitrogen and HBTU was added. The reaction mixture was stirred at 0–5° C. for 15 minutes, then warmed to room temperature and stirred an additional 2.5 hours (note 1). Water (500 ml) was added to the reaction mixture to precipitate the peptide (note 2). The resulting slurry was stirred for 45 minutes, the solids were collected by vacuum filtration, washed with water (100 ml) and dried. The solids were returned to the 2 L round bottom flask containing a magnetic stir bar and 60° C. 2-propanol (1.1 L) was added. The slurry was stirred under an atmosphere of nitrogen as it cooled to room temperature (overnight). The solids were collected by vacuum filtration and dried to give 37.5 g of FmocAA17-36NH$_2$ in 90% yield and 95.5 A % purity by HPLC (note 1).

Notes:

1 In process control, HPLC

Phenomenex Jupiter, C5, 5μ, 300 A 0.75 ml/min, 260 nm

A H$_2$O/0.05% TFA

B 50% IPA/MeOH/0.05% TFA

80–100% B over 10 min, 100% B for 25 min.

Retention time: FmocAA17-26OH, 8.2 minutes, HAA26-36NH$_2$, 8.4 minutes

Retention time: FmocAA17-36NH$_2$, 13.3 minutes

2 The reaction mixture warmed to 38° C. on addition of the water.

8.11 Preparation of Fragment H-AA(17-36)-NH$_2$

Structure:

H-Glu(OtBu)-Lys(Boc)-Asn(trt)-Glu(OtBu)-Gln(trt)-Glu(OtBu)- Leu-Leu-Glu(OtBu)-Leu-Asp(tBu)-Lys(Boc)-Trp(Boc)-Ala-Ser(tBu)-Leu-Trp(Boc)-Asn(trt)-Trp(Boc)-NH$_2$ (SEQ ID NO:19)

| | $C_{227}H_{303}N_{29}O_{44}$ HCl | | | | |
|---|---|---|---|---|---|
| Materials: | MW | eq | mmoles | grams | mL |
| FmocAA17-(17–36)-NH$_2$ | 4364.36 | 1.0 | 5.2 | 22.5 | — |
| 5 N NaOH (aq) | — | — | — | — | 55 |
| Tetrahydrofuran (THF) | — | — | — | — | 170 |
| 1 N HCl | — | — | — | — | 13 |
| Saturated NaCL (aq) | — | — | — | — | 2 × 55 |
| Heptane | — | — | — | — | 3 × 25 + 50, 200 + 50 |

Theoretical Yield 21.6 g
Expected Yield: 95–100%

Procedure:

To a 250 mL round bottom flask equipped with an air stirrer and nitrogen blanket was charged with the Fmoc-fragment synthesized in Section 8.10, above, the THF (~7.5 vol), and the 5 N NaOH(~2.5 vol). A two-phase solution was obtained and stirred at room temperature for 10–15 minutes (Note 1).

The layers were separated and the organic phase was adjusted to pH 2–3 with 1 N HCl. The solution was then washed 2×55 mL (2.5 vol) with a saturated brine solution (Note 2). The layers were separated and the organic layer was concentrated under vacuum at 15–20° C. to about ½ original volume. Heptane was added portionwise, 3×25 mL, while the concentration was continued to remove THF to a point of heavy precipitation and a final pot volume of ~100 mL (Note 2).

The product slurry was stirred at room temperature for about 2 hrs. The solids were isolated by vacuum filtration and washed with about 50 mL of heptane. The product was air dried to give 21.0 g (97.5%) of H-AA(17-36)NH$_2$.

A rework may be performed to remove residual dibenzofulvene byproduct. The product was slurried at room temperature in 200 mL of heptane for 3 hrs. The material was filtered, washed with about 50 mL of heptane, and air dried yielding 20.8 g (96.6%) of product of >95% HPLC purity.

Notes:

1) Reaction completion is monitored by HPLC:

Column: Zorbax LP C8; 1 OOA; 2011 Flow rate: 1 mL/min

Detection: UV at 260 nm

Mobile phase:

A: 0.1% aqueous TFA

B: 0.05% TFA in 1:1 ACN:IPA gradient from 80% B to 99% B in 20 minutes

Retention time: ~18 minutes

2) The solids precipitate initially as a waxy gum which remains stirrable and triturates with further concentration to a filterable solid.

9. EXAMPLE

Synthesis of Full Length T-20 peptides

Presented herein, in Sections 9.1–9.5, below, are examples of the utilization of the peptide intermediate fragments to produce full length T-20 peptides.

The Example presented in this Section demonstrates the successful coupling of solid phase and solution phase synthesis techniques to produce a full-length T-20 peptide from peptide intermediate fragments.

9.1 Preparation of Fragment AcAA1-36NH$_2$ by Solution-phase coupling of AcAA1-16OH with HAA17-36NH$_2$ The synthesis route described here represents the culmination of the T-20 four fragment approaches schematically depicted in FIGS. 1 and 3. In instances in which AcAA1-16OH is synthesized via solid phase techniques, the approach in FIG. 1 is followed, and in instances in which AcAA1-16OH is synthesized via solution phase techniques, the approach in FIG. 3 is followed. It is noted that the T-20 full length peptide synthesized here has the amino acid sequence of SEQ ID NO:1, with an acetyl modification at its amino terminus (i.e., "X") and an amido modification at its carboxyl terminus (i.e., "Z").

Structure:

Ac-Tyr(tBu)-Thr(tBu)-Ser(tBu)-Leu-Ile-His(trt)-Ser (tBu)-Leu-Ile-Glu(OtBu)-Glu(OtBu)-Ser(tBu)-Gln(trt)-Asn (trt)-Gln(trt)- Gln-Glu(OtBu)-Lys(Boc)-Asn(trt)-Glu (OtBu)-Gln(trt)-Glu(OtBu)-Leu-Leu-Glu(OtBu)-Leu-Asp (tBu)-Lys(Boc)-Trp(Boc)-Ala- Ser(tBu)-Leu-Trp(Boc)-Asn (trt)-Trp(Boc)-Phe-$NH_2$ (SEQ ID NO:1)

$C_{414}H_{543}N_{51}O_{74}$
MW 7411.95

| Materials: | MW | eq | mmoles | grams | mL |
|---|---|---|---|---|---|
| AcAA1-1OH | 3276.4 | 1 | 0.24 | 0.79 | |
| HC1HAA17-36$NH_2$ | 4178.56 | 1 | 0.24 | 1.0 | |
| HOAT | 136.1 | 1.1 | 0.26 | 0.036 | |
| HBTU | 379.25 | 1.0 | 0.95 | 0.25 | |
| $EtPr_2N$ (d = 0.755) | 129.25 | 2.8 | 0.67 | 0.087 | 0.115 |
| DMF | | | | | 20 |
| water | | | | | 25 |
| saturated NaCl | | | | | 5 |
| MTBE | | | | | 10 |
| hexane | | | | | 10 |

Theoretical Yield 1.77 g
Expected Yield: 85–100%

Procedure:

A 100 mL round bottom flask containing a magnetic stir bar was charged with AcAA1-16OH (as synthesized in either Section 7.4, above, via solid phase techniques or in Section 8.7 above, via solution phase techniques), HOAT, DMF (20 mL) then $EtPr_2N$ (0.074 mL). The solution was cooled to 0–5° C. under an atmosphere of nitrogen and HBTU was added. The solution was stirred for 15 minutes at 0–5° C. and HClHAA17-36$NH_2$ (as synthesized in Section 8.11, above) was added, followed an additional 0.041 mL of $EtPr_2N$. The cooling bath was removed and the reaction mixture was stirred for 2 hours (note 1). To precipitate the peptide, water (25 ml) and saturated aqueous sodium chloride (5 mL) was added. The solids were collected by vacuum filtration, washed with water (10 mL) and dried to give 1.74 g of crude AcAA1-36$NH_2$ (note 2). The solids were triturated with 50% MTBE/hexane at room temperature for 2.5 hours, collected by vacuum filtration and dried to give 1.70 g in 96% yield and 92 A % purity by HPLC.

Notes:

1) In process control, HPLC

Phenomenex Jupiter, C5, 5μ 300 A 0.8 mL/min, 260 nm

A $H_2O$/0.05% TFA

B 50% IPA/MeOH/0.05% TFA

80–100% B over 10 minutes, 100% B for 15 minutes

Retention time: AcAA1-16OH, 11.8 minutes.

Retention time: HCl HAA17-36$NH_2$, 12.7 minutes.

Retention time: AcAA1-36$NH_2$, 22.9 minutes.

2) The water dropout produces a very fine precipitate. A double filtration may be required.

9.2 Preparation of Fragment FmocAA1-36$NH_2$ (T-20) by Solution-phase coupling of FmocAA1-16OH with HAA17-36$NH_2$ The Example presented in this Section demonstrates the successful coupling of solid and liquid phase synthesis techniques to produce a T-20 peptide from peptide intermediate fragments. In particular, the synthesis route described here represents the T-20 three fragment approach schematically depicted in FIG. 4 to the point in the figure at which FmocAA1-36$NH_2$ is synthesized.

Structure:

Fmoc-Tyr(tBu)-Thr(tBu)-Ser(tBu)-Leu-Ile-His(trt)-Ser (tBu)-Leu-Ile-Glu(OtBu)-Glu(OtBu)-Ser(tBu)-Gln(trt)-Asn (trt)- Gln(trt)-Gln-Glu(OtBu)-Lys(Boc)-Asn(trt)-Glu (OtBu)-Gln(trt)-Glu(OtBu)-Leu-Leu-Glu(OtBu)-Leu-Asp (tBu)-Lys(Boc)-Trp(Boc)- Ala-Ser(tBu)-Leu-Trp(Boc)-Asn (trt)-Trp(Boc)-Phe-$NH_2$ (SEQ ID NO:1)

$C_{427}H_{551}N_{51}O_{75}$
MW 7593.01

| Materials: | MW | eq | mmoles | grams | mL |
|---|---|---|---|---|---|
| FmocAA1-16OH | 3453.89 | 1 | 0.12 | 0.41 | |
| HCl HAA17-36$NH_2$ | 4174.88 | 1 | 0.12 | 0.50 | |
| HOAT | 136.1 | 1.25 | 0.15 | 0.020 | |
| HBTU | 379.25 | 1.25 | 0.15 | 0.057 | |
| $EtPr_2N$ (d = 0.755) | 129.25 | 2.5 | 0.30 | 0.039 | 0.051 |
| DMF | | | | | 10 |
| water | | | | | 18 |
| 2-propanol | | | | | 14 |

Theoretical Yield 0.91 g
Expected Yield: 85–100%

Procedure:

A 25 mL round bottom flask containing a magnetic stir bar was charged with FmocAA1-16OH (as synthesized in Section 7.3, above), HCl HAA17-36$NH_2$ (as synthesized in Section 8.11, above), HOAT, DMF (10 mL) the $EtPr_2N$ was added. The solution was cooled to 0–5° C. under an atmosphere of nitrogen and HBTU was added. The reaction mixture was stirred at 0–5° C. for 15 minutes, then warmed to room temperature and stirred for 1.5 hours (note 1). Water was added to precipitate the peptide and the solids were collected by vacuum filtration and dried. The solids were triturated with 2 propanol (14 mL) for 15 hours at room temperature then water (3 mL) was added to drive the desired product from solution. The solids were collected by vacuum filtration and dried to give 0.80 g of FmocAA1-36$NH_2$ in 88% yield and 85 A % HPLC purity.

Notes:

1) In process control, HPLC

Phenomenex Jupiter, C5, 5μ, 300 A 0.8 mL/min, 260 nm

A $H_2O$/0.05% TFA

B 50% IPA/MeOH/0.05% TFA

80–100% B over 10 minutes, 100% B for 15 minutes

Retention time: FmocAA1-16OH, 11.4 minutes.

Retention time: HCl HAA17-36$NH_2$, 12. minutes.

Retention time: FmocAA1-36$NH_2$, 20.4 minutes.

TLC, 9/1 dichloromethane/ethanol

UV, Iodine detection

Rft: FmocAA1-36$NH_2$, 0.71.

9.3 Preparation of Fragment HAA1-36$NH_2$ (T-20)

The Example presented in this Section demonstrates the successful coupling of solid and liquid phase synthesis techniques to produce a T-20 peptide from peptide intermediate fragments. In particular, the synthesis route described here represents the T-20 three fragment approach schematically depicted in FIG. 4 to the point in the figure at which H-AA1-36-NH$_2$ is synthesized.

Structure:

H-Tyr(tBu)-Thr(tBu)-Ser(tBu)-Leu-Ile-His(trt)-Ser(tBu)-Leu-Ile-Glu(OtBu)-Glu(OtBu)-Ser(tBu)-Gln(trt)-Asn(trt)-Gln(trt)- Gln-Glu(OtBu)-Lys(Boc)-Asn(trt)-Glu(OtBu)-Gln(trt)-Glu(OtBu)-Leu-Leu-Glu(OtBu)-Leu-Asp(tBu)-Lys(Boc)-Trp(Boc)-Ala- Ser(tBu)-Leu-Trp(Boc)-Asn(trt)-Trp(Boc)-Phe-NH$_2$ (SEQ ID NO:1)

| Materials: | $C_{412}H_{541}N_{51}O_{73}$ MW 7370.94 | | | | |
|---|---|---|---|---|---|
| | MW | eq | mmoles | grams | mL |
| FmocAA1-36NH$_2$ | 7593.01 | 1 | 0.105 | 0.80 | |
| piperidine | | | | | 0.5 |
| DMF | | | | | 9.5 |
| water | | | | | 20 |
| saturated aqueous NaCl | | | | | 5 |
| MTBE | | | | | 5 |
| hexane | | | | | 5 |

Theoretical Yield .77 g
Expected Yield: 85–95%

Procedure:

A 25 mL round bottom flask containing a magnetic stir bar was charged with FmocAA1-36NH$_2$ (as synthesized in Section 9.2, above), DMF (9.5 mL) and piperidine (0.5 mL). The solution was stirred at room temperature under an atmosphere of nitrogen for 2 hours (note 1, 2). Water (20 mL) and saturated aqueous sodium chloride (5 mL) was added to precipitate the protected peptide. The solids were collected by vacuum filtration and dried to give 0.77 g of HAA1-36NH$_2$ contaminated with fulvene and the piperidine-fulvene adduct. The solids were triturated with 50% MTBE/hexane at room temperature for 15 hours to remove the fulvene and the piperidine-fulvene adduct. The solids were collected by vacuum filtration and dried to give 0.73 g of HAA1-36NH$_2$ in 95% yield and 90 A % purity by HPLC.

Notes:
1) In process control, HPLC

Phenomenex Jupiter, C5, 5$\mu$, 300 A 0.8 mL/min, 260 nm

A H$_2$O/0.05% TFA

B 50% IPA/MeOH/0.05% TFA

80–100% B over 10 minutes, 100% B for 15 minutes

Retention time: FmocAA1-36OH, 20.4 minutes.

Retention time: HCl HAA1-36NH$_2$, 19.9 minutes

Retention time: fulvene and piperidine-fulvene adduct, 5 minutes.

TLC, 9/1 dichloromethane/ethanol

UV, Iodine detection

Rt: FmocAA1-36NH$_2$, 0.71.

2) The product and starting material do not separate well on TLC or reverse phase HPLC. Product formation was followed by observing the fulvene and piperidiine-fulvene adduct.

9.4 Preparation of Fragment AcAA1-36NH$_2$ (T-20) by N-terminal acetylation of HAA1-36NH$_2$ The Example presented in this Section demonstrates the successful coupling of solid and liquid phase synthesis techniques to produce a T-20 peptide from peptide intermediate fragments. In particular, the synthesis route described here represents the T-20 three fragment approach schematically depicted in FIG. 4 to the point in the figure at which Ac-AA1-36-NH$_2$ is synthesized.

Structure:

Ac-Tyr(tBu)-Thr(tBu)-Ser(tBu)-Leu-Ile-His(trt)-Ser(tBu)-Leu-Ile-Glu(OtBu)-Glu(OtBu)-Ser(tBu)-Gln(trt)- Asn(trt)-Gln(trt)-Gln-Glu(C)tBu)-Lys(Boc)-Asn(trt)-Glu(OtBu)-Gln(trt)-Glu(OtBu)-Leu-Leu-Glu(OtBu)-Leu- Asp(tBu)-Lys(Boc)-Trp(Boc)-Ala-Ser(tBu)-Leu-Trp(Boc)-Asn(trt)-Trp(Boc)-Phe-NH$_2$ (SEQ ID NO:1)

| Materials: | $C_{414}H_{543}N_{51}O_{74}$ MW 7411.95 | | | | |
|---|---|---|---|---|---|
| | MW | eq | mmoles | grams | mL |
| HAA1-36NH$_2$ | 7370.94 | 1 | 0.096 | 0.71 | |
| acetic anhydride (d = 1.08) | 102.09 | 3 | 0.29 | 0.029 | 0.027 |
| pyridine (d = 0.978) | 79.1 | 6 | 0.58 | 0.046 | 0.046 |
| DMF | | | | | 10 |
| water | | | | | 17.5 |
| saturated aqueous NaCl | | | | | 7.5 |

Theoretical Yield 0.71 g
Expected Yield: 85–100%

Procedure:

A 25 mL round bottom flask containing a magnetic stir bar was charged with HAA1-36NH$_2$ (as synthesized in Section 9.3, above), DMF (10 mL), pyridine (0.046 mL) and acetic anhydride (0.027 mL) (note 1). The solution was stirred at room temperature under an atmosphere of nitrogen for 4 hours (note 2). Water (7.5 mL) and saturated aqueous sodium chloride (7.5 mL) was added to precipitate the protected peptide. The solids were collected by vacuum filtration, washed with water (10 mL) and dried to give 0.65 g of AcAA1-36NH$_2$ in 91% yield and 90 A % purity by HPLC (note 3).

Notes:
1) Dichloromethane may be also utilized as the solvent for this reaction.

2) In process control, HPLC

Phenomenex Jupiter, C5, 5$\mu$, 300 A 0.8 mL/min, 260 nm

A H$_2$O/0.05% TFA

B 50% IPA/MeOH/0.05% TFA

80–100% B over 10 minutes, 100% B for 15 minutes

Retention time: HAA1-36OH, 23.3 minutes.

Retention time: AcAA1-36NH$_2$, 22.7 minutes.

3) The product and starting material do not separate well on TLC or reverse phase HPLC.

9.5 Preparation of T-20 Side by Side-chain deprotection of AcAA1-36NH$_2$

The Example presented in this Section demonstrates the successful coupling of solid and liquid phase synthesis techniques to produce a T-20 peptide from peptide intermediate fragments. In particular, the synthesis route described here represents the T-20 three fragment approach shown in FIG. 4.

Structure:

Ac-Tyr-Thr-Ser-Leu-Ile-His-Ser-Leu-Ile-Glu-Glu-Ser-Gln-Asn-Gln-Gln-Glu-Lys-Asn-Glu-Gln-Glu-Leu-LeuGlu-Leu-Asp-Lys-Trp- Ala-Ser-Leu-Trp-Asn-Trp-Phe-NH$_2$ (SEQ ID NO:1)

| $C_{414}H_{543}N_{51}O_{74}$ MW 4492.1 | | | | |
|---|---|---|---|---|
| Materials: | MW | eq | mmoles | grams | mL |
| AcAA1-36NH$_2$ | 7411.95 | 1 | 0.035 | 0.26 | |
| Trifluoroacetic acid | | | | | 2.25 |
| Water | | | | | 15.1 |
| Dithiothreitol | | | 0.12 | | |
| MTBE | | | | | 170 |
| Acetonitrile | | | | | 15 |

Theoretical Yield 157 mg
Expected Yield: 25–50%

Procedure:

A solution of 90:5:5 (v/v/wt %) trifluoroacetic acid/water/dithiothreitol was degassed with nitrogen and cooled to 0–5° C. To the cooled solution was added AcAA1-36NH$_2$ (as synthesized in Section 9.4, above). The slurry was stirred at 0–5° C. until the solids dissolved (~5 minutes) then warmed to room temperature and stirred for 2.5 hours. The solution was added to 0–5° C. MTBE (70 mL) to precipitate the peptide. The slurry was spun in a centrifuge for five minutes at 2200 rpm and the MTBE decanted from the solids. The solids were again suspended in MTBE (50 mL), spun in a centrifuge for five minutes at rpm and the MTBE was decanted. This process was repeated once more then the solids were dissolved in 1:1 water/acetonitrile (30 mL) containing 1 vol % acetic acid and stored at room temperature for 24 hours (note 1). The solution was frozen then freeze dried using a lyopholyzer to give 155 mg of crude T-20. Purification by preparative HPLC provides 55 mg of the full-length T-20 peptide in 95 A % purity by HPLC (note 2).

Notes:
1) The tBu side-chain of Trp(Boc) is removed quickly leaving TrpCOOH. Decarboxylation of the TrpCOOH requires a minimum of 24 hours at ambient temperature in aqueous acetic acid.
2) Preparative HPLC
   2" YMC, 120 A, 10µ, C18
   220 nm, 50 mL/min
   A H$_2$O/0–1% TFA
   B ACN/0.1% TFA
   39–49% B/40 minutes

10. EXAMPLE

Purification of T-20 PEPTIDE

The Example presented herein describes methods by which T-20 and T-20-like peptides can be purified under conditions which greatly increase peptide purification throughput.

Materials

Column used: 20×30 cm packed with Amberchrom CG-300S (Tosohaus; Montgomeryville, Pa.) 35 µm particles.

Preparat ion of Buffers

Buffer A=100 mM Ammonium acetate adjusted to pH 8.5 with NH$_4$OH.

Buffer B=acetonitrile.

1. Column with approximately 6 column volumes of 20% B.
2. T-20 is dissolved in 50–100 mL of 85% A/15% B per gram of peptide. The pH is adjusted to 8–10 with 2M K$_2$CO$_3$. The acetonitrile concentration in the T-20 sample does not exceed 15–20%.
3. T-20 solution is loaded at 500 mL/min, with column pressure monitoring.
4. After T-20 solution is loaded, a 3 column volume (10 L) of a solution of 80% A/15% B is loaded to wash out lines.
5. Column eluate is monitored at 303 mn, and eluate is collected during entire loading process. The wavelength or attenuation is adjusted during the run to keep peak on scale. Absorbance is a function of wavelength and cell path length.
6. Gradient operation is begun as below (1.6% change in B/hour), with pressure being monitored during entire run.

| Time (min) | % B | Flow (mL/min) |
|---|---|---|
| 0 | 15 | 330 |
| 788 | 36 | 330 |

7. 10 min fractions are collected (3.3 L) when main peak begins to elute. All of T-20 should be eluted by 35% B. On average, 35–40 fractions are collected. Fractions are stored at 0–5° C. until a determination of which fraction to pool is made.
8. Fractions are collected until detector absorbance is <0.1 AU or until a major inflection point is reached after the main peak elutes.
9. The purity of each fraction is monitored by analytical reversed-phased HPLC.

Results

T-20 peptide is much more soluble at pH ranges greater than >7. Column supports commonly used to purify peptides are silica-based and can, therefore, only be used at pH ranges because silica support tends to dissolve at higher pH ranges.

The method described herein utilizes a polystyrene-based resin support that is stable at a broad pH range (pH 1–14). This method greatly increases the capacity of the column in that T-20 throughput increased from 10 g up to 250–450 g (for an 8" diameter×30 cm column).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for the synthesis of a peptide having the formula

Ac-YTSLIHSLIEESQNQQEKNEQELLELDKWA
SLWNWF-NH$_2$ (SEQ ID NO:1), comprising:
 (a) reacting a side-chain protected peptide of the formula:
   Fmoc-EKNEQELLEL-COOH (SEQ ID NO:11) with a side chain-protected peptide of the formula:

NH$_2$-DKWASLWNWF-NH$_2$ (SEQ ID NO:18)

to yield a side-chain protected peptide of the formula:

Fmoc-EKNEQELLELDKWASLWNWF-NH$_2$ (SEQ ID NO:12);

(b) deprotecting the amino terminus of the peptide produced in (a);
 (c) reacting the peptide produced in (b) with a side-chain protected peptide of the formula:

Fmoc-YTSLIHSLIEESQNQQ-COOH (SEQ ID NO:4)

to yield a side-chain protected peptide of the formula:

Fmoc-YTSLIHSLIEESQNQQEKNEQELLELDKWASLWNWF-NH$_2$ (SEQ ID NO:1);

(d) modifying the amino terminus of the peptide produced in (c) into an acetyl modification; and
 (e) deprotecting the side chains of the side-chain protected peptide of (d) to yield a peptide of the formula:

Ac-YTSLIHSLIEESQNQQEKNEQELLELDKWA
   SLWNWF-NH$_2$ (SEQ ID NO:1).

2. A method for the synthesis of a peptide having the formula

Ac-YTSLIHSLIEESQNQQEKNEQELLELDKWA
SLWNWF-NH$_2$ (SEQ ID NO:1), comprising:
 (a) reacting a side-chain protected peptide of the formula:
   Fmoc-EKNEQELLEL-COOH (SEQ ID NO:11) with a side chain-protected peptide of the formula:

NH$_2$-DKWASLWNWF-NH$_2$ (SEQ ID NO:18)

to yield a side-chain protected peptide of the formula:

Fmoc-EKNEQELLELDKWASLWNWF-NH₂ (SEQ ID NO:12);

(b) deprotecting the amino terminus of the peptide produced in (a);

(c) reacting the peptide produced in (b) with a side-chain protected peptide of the formula:

Ac-YTSLIHSLIEESQNQQ-COOH (SEQ ID NO:4)

to yield a side-chain protected peptide of the formula:

Ac-YTSLIHSLIEESQNQQEENEQELLELDKWASLW
NWF-NH₂ (SEQ ID NO:1);

and (d) deprotecting the side chains of the side-chain protected peptide of (c) to yield a peptide of the formula:

Ac-YTSLIHSLIEESQNQQEKNEQELLELDKWASLW
NWF-NH₂ (SEQ ID NO:1).

3. A method for the synthesis of a peptide of the formula:

X-YTSLIHSLIEESQNQQEKNEQELLELDKWASLW
NWF-Z (SEQ ID NO:1), comprising:

(a) reacting a side-chain protected peptide of the formula:

EKNEQELLELDKWASLWNWF-Z (SEQ ID NO:12), wherein the amino terminus is deprotected;
with a side-chain protected peptide of the formula:

X-YTSLIHSLIEESQNQQ-COOH (SEQ ID NO:4), to yield a side-chain protected peptide of the formula:

X-YTSLIHSLIEESQNQQEKNEQELLELDKWASLW
NWF-Z (SEQ ID NO:1);

wherein X is a protecting group, an acetyl group or a macromolecular carrier group selected from the group consisting of lipid fatty acid conjugates, polyethylene glycol and carbohydrates; and
wherein Z is a protecting group, an amido group, or a macromolecular carrier group selected from the group consisting of lipid fatty acid conjugates, polyethylene glycol and carbohydrates.

4. The method of claim 3, wherein X is a protecting group selected from the group consisting of 9-fluoroenylmethoxycarbonyl (Fmoc), t-butyl (t-Bu), trityl (trt), t-butyloxycarbonyl (Boc), carbobenzoxyl, dansyl and a para-nitrobenzyl ester group.

5. The method of claim 3, wherein Z is a protecting group selected from the group consisting of 9-fluoroenylmethoxycarbonyl (Fmoc), t-butyl (t-Bu), trityl (trt), t-butyloxycarbonyl (Boc), carbobenzoxyl, dansyl and a para-nitrobenzyl ester group.

6. The method of claim 3 which further comprises deprotecting the side chains of the side-chain protected peptide of the formula:

X-YTSLIHSLIEESQNQQEKNEQELLELDKWASLW
NWF-Z (SEQ ID NO: 1).

7. The method of claim 3 or 6 wherein X is an acetyl group.

8. The method of claim 7 wherein Z is an amido group.

9. The method of claim 3 or 6 wherein X is a protecting group and wherein the method further comprises the step of modifying X into an acetyl group.

10. The method of claim 9, wherein Z is an amido group.

11. The method of claim 3 wherein the side-chain protected peptide of the formula:

X-YTSLIHSLIEESQNQQ-COOH (SEQ ID NO: 4)

is synthesized by a method comprising:

(a) reacting a side-chain protected peptide of the formula:

IEESQNQQ-OPNB (SEQ ID NO:7), wherein OPNB represents a para-nitro benzyl ester group, and wherein the amino terminus is deprotected;
with a side-chain protected peptide of the formula:

X-YTSLIHSL-COOH (SEQ ID NO:4)

(b) deprotecting the carboxy terminus of the peptide produced in (a) to yield the side-chain protected peptide of the formula:

X-YTSLIHSLIEESQNQQ-COOH (SEQ ID NO:4).

12. The method of claim 11 wherein the carboxy terminus of the peptide produced in (a) is deprotected by palladium-catalyzed hydrogenolysis.

13. The method of claim 11 wherein the side-chain protected peptide of the formula:

IEESQNQQ-OPNB (SEQ ID NO:7)

is synthesized by a method comprising:

reacting a side-chain protected peptide of the formula:

IEESQNQ-COOH (SEQ ID NO:6)

with the para-nitro benzyl ester of glutamine (HGlnOPNB), to yield the side-chain protected peptide of the formula:

IEESQNQQ-OPNB (SEQ ID NO:7).

14. The method of claim 3, wherein the side-chain protected peptide of the formula:

X-YTSLIHSLIEESQNQQ-COOH (SEQ ID NO:4), is synthesized by solid phase peptide synthesis.

15. The method of claim 3 wherein the side-chain protected peptide of the formula:

EKNEQELLELDKWASLWNWF-Z (SEQ ID NO:12)

is synthesized by a method comprising:

reacting a side-chain protected peptide of the formula:

DKWASLWNW-Z (SEQ ID NO:18), wherein the amino terminus is deprotected;
with a side-chain protected peptide of the formula:

EKNEQELLEL-COOH (SEQ ID NO:11)

to yield the side-chain protected peptide of the formula:

EKNEQELLELDKWASLWNW-Z (SEQ ID NO:12).

16. The method of claim 15 wherein the side-chain protected peptide of the formula:

DKWASLWNWF-Z (SEQ ID NO:18)

is synthesized by a method comprising:
reacting a side-chain protected peptide of the formula:

DKWASLWNW-COOH (SEQ ID NO:17)

with phenylalanine amide to yield the side-chain protected peptide of the formula:

DKWASLWNWF-Z (SEQ ID NO:18).

17. The method of claim 3, wherein the side-chain protected peptide of the formula:

EKNEQELLELDKWASLWNWF-Z (SEQ ID NO:12)

is synthesized by a method comprising:
reacting a side-chain protected peptide of the formula:

LELDKWASLWNWF-Z (SEQ ID NO:16);

wherein the amino terminus id deprotected with a side-chain protected peptide of the formula:

AEKNEQEL-COOH (SEQ ID NO:10)

to yield a side-chain protected peptide of the formula:

EKNEQELLELDKWASLWNWF-Z (SEQ ID NO:12).

18. The method of claim 17, wherein the side-chain protected peptide of the formula:

LELDKWASLWNWF-Z (SEQ ID NO:16)

is synthesized by a method comprising:
reacting a side-chain protected peptide of the formula:

LELDKWASLWNW-COOH (SEQ ID NO:15)

with phenylalanine amide to yield a side-chain protected peptide of the formula:

LELDKWASLWNWF-Z (SEQ ID NO:16).

19. The method of claim 3 wherein the side-chain protected peptide of the formula:

EKNEQELLELDKWASLWNWF-Z (SEQ ID NO:12)

is synthesized by a method comprising:
reacting a side-chain protected peptide of the formula:

EKNEQELLELDKWASLWNW-COOH (SEQ ID NO:19)

with phenylalanine amide, to yield a side-chain protected peptide of the formula:

EKNEQELLELDKWASLWNWF-Z (SEQ ID NO:12).

20. A method of claim 19 wherein the side-chain protected peptide of the formula:

EKNEQELLELDKWASLWNW-COOH (SEQ ID NO:19)

is synthesized by a method comprising:
reacting a side-chain protected peptide of the formula:

DKWASLWNW-COOH (SEQ ID NO:17), wherein the amino terminus is deprotected; with a side-chain protected peptide of the formula:

EKNEQELLEL-COOH (SEQ ID NO:11)

to yield a side-chain protected peptide of the formula:

EKNEQELLELDKWASLWNW-COOH (SEQ ID NO:19).

21. The method of claim 19, wherein the side-chain protected peptide of the formula:

EKNEQELLELDKWASLWNW-COOH (SEQ ID NO:19)

is synthesized by a method comprising:
reacting a side-chain protected peptide of the formula:

LELDKWASLWNW-COOH (SEQ ID NO:15), wherein the amino terminus is deprotected;
with a side-chain protected peptide of the formula:

EKNEQEL-COOH (SEQ ID NO:10), to yield a side-chain protected peptide of the formula:

EKNEQELLELDKWASLWNW-COOH (SEQ ID NO:19).

22. The method of claim 7, wherein the side-chain protected peptide of the formula:

Ac-YTSLIHSLIEESQNQQ-COOH (SEQ ID NO:4), is synthesized by a method comprising:
(a) acetylating a side-chain protected peptide of the formula:

YTSLIHSLIEESQNQQ-OPNB (SEQ ID NO:4), wherein OPNB represents a para-nitro benzyl ester group, and wherein the amino terminus is deprotected, to yield a side-chain protected peptide of the formula:

Ac-YTSLIHSLIEESQNQQ-OPNB (SEQ ID NO:4);

(b) deprotecting the carboxy terminus of the peptide produced in (a), to yield a side-chain protected peptide of the formula:

Ac-YTSLIHSLIEESQNQQ-COOH (SEQ ID NO:4).

23. The method of claim 22, wherein said acetylating is accomplished by reacting the side-chain protected peptide of the formula:

YTSLIHSLIEESQNQQ-OPNB (SEQ ID NO:4)

with acetic anhydride.

24. The method of claim 22, wherein the side-chain protected peptide of the formula:

YTSLIHSLIEESQNQQ-OPNB (SEQ ID NO:4)

is synthesized by a method comprising:
reacting a side-chain protected peptide of the formula:

IEESQNQQ-OPNB (SEQ ID NO:7), wherein the amino terminus is deprotected;

with a side-chain protected peptide of the formula:

YTSLIHSL-COOH (SEQ ID NO:2), to yield the side-chain protected peptide of the formula:

YTSLIHSLIEESQNQQ-OPNB (SEQ ID NO:4).

25. A method for the synthesis of a peptide of the formula:

X-YTSLIHSLIEESQNQQEKNEQELLELDKWASLW
NWF-Z (SEQ ID NO:1), comprising:
(a) reacting a side-chain protected peptide of the formula:

QEKNEQELLELDKWASLWNWF-Z (SEQ ID NO:9), wherein the amino terminus deprotected;
with a side-chain protected peptide of the formula:

X-YTSLIHSLIEESQNQ-COOH (SEQ ID NO:3), to yield a side-chain protected peptide of the formula:

X-YTSLIHSLIEESQNQQEKNEQELLELDKWASLW
NWF-Z (SEQ ID NO:1);

wherein Z is a protecting group, an acetyl group or a macromolecular carrier group selected from the group consisting of lipid fatty acid conjugates, polyethylene glycol and carbohydrates; and Z is a protecting group, an amido group or a macromolecular carrier group selected from the group consisting of lipid fatty acid conjugates, polyethylene glycol and carbohydrates.

26. The method of claim 25 wherein X is a protecting group selected from the group consisting of 9-fluoroenylmethoxy-carbonyl (Fmoc), t-butyl (t-Bu), trityl (trt), t-butyloxycarbonyl (Boc), carbobenzoxyl, dansyl and a para-nitrobenzyl ester group.

27. The method of claim 25, wherein Z is a protecting group selected from the group consisting of 9-fluoroenylmethoxy-carbonyl (Fmoc), t-Bu), trityl (trt), t-butyloxycarbonyl (Boc), carbobenzoxyl, dansyl and a para-nitrobenzyl ester group.

28. The method of claim 25 which further comprises deprotecting the side chains of the side-chain protected peptide of the formula:

X-YTSLIHSLIEESQNQQEKNEQELLELDKWASLW
NWF-Z (SEQ ID NO:1).

29. The method of claim 25 or 28 wherein X is an acetyl group.

30. The method of claim 29 wherein Z is an amido group.

31. The method of claim 25 or 28 wherein X is a protecting group and wherein the method further comprises the step of modifying X into an acetyl group.

32. The method of claim 31, wherein Z is an amido group.

33. The method of claim 25 wherein the side-chain protected peptide of the formula:

QEKNEQELLELDKWASLWNWF-Z (SEQ ID NO:9), is synthesized by a method comprising:
reacting a side-chain protected peptide of the formula:

QEKNEQELLELDKWASLWNW-Z (SEQ ID NO:8)

with phenylalanine amide, to yield the side chain protected peptide of the formula:

QEKNEQELLELDKWASLWNWF-Z (SEQ ID NO:9).

34. The method of claim 25, wherein the side-chain protected peptide of the formula:

X-YTSLIHSLIEESQNQ-COOH (SEQ ID NO:3)

is synthesized by solid phase peptide synthesis.

35. A method for the synthesis of a peptide of the formula:

XYTSLIHSLIEESQNQQEKNEQELLELDKWASLW
NWF-Z (SEQ ID NO:1), comprising:
(a) reacting a side-chain protected peptide of the formula:

NEQELLELDKWASLWNWF-Z (SEQ ID NO:14), wherein the amino terminus is deprotected;
with a side-chain protected peptide of the formula:

X-YTSLIHSLIEESQNQQEK-COOH (SEQ ID NO:5), wherein R is a protecting group; to yield a side-chain protected peptide of the formula:

X-YTSLIHSLIEESQNQQEKNEQELLELDKWASLW
NWF-Z (SEQ ID NO:1);

wherein X is a protecting group, an acetyl group, or a macromolecular carrier group selected from the group consisting of lipid fatty acid conjugates, polyethylene glycol and carbohydrates; and
wherein Z is a protecting group, an amido group or a macromolecular carrier group selected from the group consisting of lipid fatty acid conjugates, polyethylene glycol and carbohydrates.

36. The method of claim 35, wherein X is a protecting group selected from the group consisting of 9-fluoroenylmethoxy-carbonyl (Fmoc), t-butyl (t-Bu), trityl (trt), t-butyloxycarbonyl (Boc), carbobenzoxyl, dansyl and para-nitrobenzyl ester group.

37. The method of claim 35, wherein Z is a protecting group selected from the group consisting of 9-fluoroenylmethoxy-carbonyl (Fmoc), t-butyl (t-Bu), trityl (trt), t-butyloxycarbonyl (Boc), carbobenzoxyl, dansyl and para-nitrobenzyl ester group.

38. The method of claim 35, which further comprises deprotecting the side chains of the side-chain protected peptide of the formula:

X-YTSLIHSLIEESQNQQEKNEQELLELDKWASLW
NWF-Z (SEQ ID NO:1).

39. The method of claim 35 or 38 wherein X is an acetyl group.

40. The method of claim 39 wherein Z is an amido group.

41. The method of claim 35 or 38 wherein X is a protecting group and wherein the method further comprises the step of modifying X into an acetyl group.

42. The method of claim 41 wherein Z is an amido group.

43. The method of claim 35, wherein the side-chain protected peptide of the formula:

NEQELLELDKWASLWNWF-Z (SEQ ID NO:14), is synthesized by a method comprising:
  reacting a side-chain protected peptide of the formula:

NEQELLELDKWASLWNW-Z        (SEQ ID NO:13)

with phenylalanine amide, to yield the side-chain protected peptide of the formula:

NEQELLELDKWASLWNWF-Z       (SEQ ID NO:14).

44. The method of claim 35 wherein the side-chain protected peptide of the formula:

X-YTSLIHSLIEESQNQQEK-COOH        (SEQ ID NO: 5)

is synthesized by solid phase peptide synthesis.

* * * * *